United States Patent
Cheng et al.

(10) Patent No.: US 7,109,222 B2
(45) Date of Patent: Sep. 19, 2006

(54) COMPOUNDS THAT MODULATE PPAR ACTIVITY AND METHODS OF PREPARATION

(75) Inventors: Xue-Min Cheng, Ann Arbor, MI (US); Gary F. Filzen, Ann Arbor, MI (US); Andrew G. Geyer, Novi, MI (US); Chitase Lee, Ann Arbor, MI (US); Bharat K. Trivedi, Farmington Hills, MI (US)

(73) Assignee: Warner-Lambert Company, LLC, Morris Plains, NJ (US)

( * ) Notice: Subject to any disclaimer, the term of this patent is extended or adjusted under 35 U.S.C. 154(b) by 0 days.

(21) Appl. No.: 11/025,271

(22) Filed: Dec. 24, 2004

(65) Prior Publication Data

US 2005/0107442 A1    May 19, 2005

Related U.S. Application Data

(62) Division of application No. 10/324,266, filed on Dec. 19, 2002, now Pat. No. 6,867,224.

(60) Provisional application No. 60/362,411, filed on Mar. 7, 2002.

(51) Int. Cl.
*A61K 31/426* (2006.01)
*C07D 277/30* (2006.01)

(52) U.S. Cl. .................. 514/365; 548/203; 548/202

(58) Field of Classification Search ................ 514/365; 548/203, 202
See application file for complete search history.

(56) References Cited

FOREIGN PATENT DOCUMENTS

| WO | WO 97/28149 A1 | 8/1997 |
|---|---|---|
| WO | WO 01/00603 A1 | 1/2001 |
| WO | WO 01/16120 A1 | 3/2001 |
| WO | WO 01/92250 A2 | 12/2001 |
| WO | WO 01/94335 A2 | 12/2001 |
| WO | WO 02/16331 A1 | 2/2002 |
| WO | WO 02/18355 A1 | 3/2002 |
| WO | WO 02/096904 A1 | 12/2002 |
| WO | WO 02/100403 A1 | 12/2002 |
| WO | WO 02/102780 A1 | 12/2002 |
| WO | WO 03/011842 A | 2/2003 |

OTHER PUBLICATIONS

T. Gordon et al., The American Journal of Medicine, 1977;62:707-714.
G. Romussi et al., J. Heterocyclic Chem., 13, 211 (1976).
W.R. Oliver et al., PNAS, vol. 98, pp. 5306-5311, (2001).
S.M. Berge et al., "Pharmaceutical Salts", Journal of Pharmaceutical Sciences, 1977;66:1-19.

*Primary Examiner*—Joseph K. McKane
*Assistant Examiner*—Robert Shiao
(74) *Attorney, Agent, or Firm*—Charles W. Ashbrook; Michelle A. Sherwood

(57) ABSTRACT

This invention discloses compounds that alter PPAR activity. The invention also discloses pharmaceutically acceptable salts of the compounds, pharmaceutically acceptable compositions comprising the compounds or their salts, and methods of using them as therapeutic agents for treating or preventing hyperlipidemia and hypercholesteremia in a mammal. The present invention also discloses method for making the disclosed compounds.

8 Claims, No Drawings

COMPOUNDS THAT MODULATE PPAR ACTIVITY AND METHODS OF PREPARATION

CROSS REFERENCE TO RELATED APPLICATION

This application is a divisional application of U.S. Ser. No. 10/324,266, filed Dec. 19, 2002, now U.S. Pat. No. 6,867,224, which claims priority to U.S. Provisional Application Ser. No. 60/362,411 filed Mar. 7, 2002.

FIELD OF THE INVENTION

The present invention relates to compounds and pharmaceutical formulations that can be used to treat conditions mediated by nuclear receptors, more specifically, to compounds and pharmaceutical formulations that modulate PPAR activity.

BACKGROUND OF THE INVENTION

Hypercholesterolemia, hyperlipidemia, and diabetes are well recognized risk factors in the onset of atherosclerosis and coronary heart disease. Hypercholesterolemia and hyperlipidemia are characterized by excessively high levels of blood cholesterol and lipids. The blood cholesterol pool is generally dependent on dietary uptake of cholesterol from the intestine and biosynthesis of cholesterol throughout the body, especially the liver. The majority of cholesterol in plasma is carried on apolipoprotein B-containing lipoproteins, such as low-density lipoproteins (LDL) and very-low-density lipoproteins (VLDL). The risk of coronary artery disease in man increases when LDL and VLDL levels increase. Conversely, high levels of cholesterol carried in high-density lipoproteins (HDL) is protective against coronary artery disease (Am. J. Med., 1977; 62:707–714).

The statins represent perhaps the most important class of lipid-lowering drugs. These compounds inhibit HMG-CoA reductase which is implicated in the rate-limiting step in cellular cholesterol biosynthesis. Representative statins include atorvastatin, lovastatin, pravastatin, and simvastatin. The effectiveness of these compounds depends on LDL receptor regulation. Other important antilipidemia drugs include fibrates such as gemfibril and clofibrate, bile acid sequestrants such as cholestyramine and colestipol, probucol, and nicotinic acid analogs.

To date, a number of oral antidiabetic agents have been developed. The most commonly used hypoglygemic drugs are the sulfonylureas. Sulfonylureas are generally used to stimulate insulin. The biguanide metformin is generally used to improve insulin sensitivity and to decrease hepatic glucose output. Acarbose is used to limit postprandial hyperglycemia. Thiazolidine 2,4 diones are used to enhance insulin action without increasing insulin secretion.

Peroxisome Proliferator Activation Receptors (PPAR) are implicated in a number of biological processes and disease states including hypercholesterolemia, hyperlipidemia, and diabetes. PPARs are members of the nuclear receptor superfamily of transcription factors that includes steroid, thyroid, and vitamin D receptors. They play a role in controlling expression of proteins that regulate lipid metabolism. Furthermore, the PPARs are activated by fatty acids and fatty acid metabolites. There are three PPAR subtypes PPARα, PPARβ (also referred to as PPARδ), and PPARγ. Each receptor shows a different pattern of tissue expression, and differences in activation by structurally diverse compounds.

PPARγ, for instance, is expressed most abundantly in adipose tissue and at lower levels in skeletal muscle, heart, liver, intestine, kidney, vascular endothelial and smooth muscle cells as well as macrophages. PPAR receptors are associated with regulation of insulin sensitivity and blood glucose levels, macrophage differentiation, inflammatory response, and cell differentiation. Accordingly, PPARs have been associated with obesity, diabetes, carcinogenesis, hyperplasia, atherosclerosis, hyperlipidemia, and hypercholesterolemia.

In addition, PPARα agonists lower plasma triglycerides and LDL cholesterol and are therefore useful in treating hypertriglyceridemia, hyperlipidemia and obesity. PPARγ is associated with the development of non-insulin-dependent diabetes mellitus (NIDDM), hypertension, coronary artery disease, hyperlipidemia and certain malignancies. Finally, activation of PPARβ has been demonstrated to increase HDL levels. (Leibowitz, WO97/28149, August 1997.) More recently, a PPARβ selective agonist was reported to have shown a dose-related increase in serum HDL-C and decrease in LDL-C and VLDL-TG in insulin-resistant middle aged rhesus monkeys. (W. R. Oliver et al., PNAS, v. 98, pp. 5306–5311, 2001)

Antilipidemic and antidiabetic agents are still considered to have non-uniform effectiveness. The effectiveness of antidiabetic and antilipidemic therapies is limited, in part because of poor patient compliance due to unacceptable side effects. These side effects include diarrhea and gastrointestinal discomfort, and in the case of antidiabetics, edema, hypoglycemia and hepatoxicity. Furthermore, each type of drug does not work equally well in all patients.

For the reasons set forth above, there is a need for novel antilipidemic and antidiabetic agents that can be used alone or in combination. Furthermore, activation of PPARβ alone or in combination with the simultaneous activation of PPARα and/or PPARγ may be desirable in formulating a treatment for hyperlipidemia in which HDL is increased and LDL lowered.

SUMMARY OF THE INVENTION

The present invention provides compounds capable of modulating PPAR activity. Compounds of the present invention are described by Formula 1:

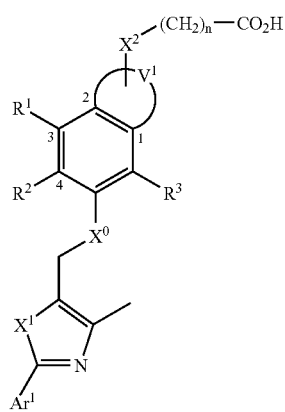

or a pharmaceutically acceptable salt thereof, where:

$V^1$ is a saturated or unsaturated, substituted or unsubstituted hydrocarbon chain or hydrocarbon-heteroatom chain having from 3 to 6 atoms wherein the carbon atom of position 1 is connected to the carbon atom of position 2 to form a five to eight member ring where the

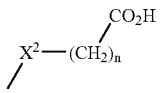

is attached to a substitutionally available position of said ring;

$X^0$ and $X^1$ are independently O or S;

$X^2$ is absent, O, S, or $NR^4$;

$Ar^1$ is substituted or unsubstituted aryl or heteroaryl;

$R^1$, $R^2$, and $R^3$ are independently hydrogen, lower alkyl, lower alkoxy, lower thioalkoxy, $-O(CH_2)_pCF_3$, halogen, nitro, cyano, $-OH$, $-SH$, $-CF_3$, $S(O)_p$Alkyl, $S(O)_p$Aryl, $-(CH_2)_mOR^4$, or $-(CH_2)_mNR^5R^6$, $COR^4$, $-CO_2H$, $-CO_2R^4$, or $-NR^5R^6$ or R1 and R2 are joined together to form a substituted or unsubstituted, saturated or unsaturated cyloalkyl or heterocycloalkyl ring;

$R^4$ is hydrogen, alkyl, alkenyl, alkynyl, or aryl;

$R^5$ and $R^6$ are independently hydrogen, alkyl, alkenyl, alkynyl, cycloalkyl, $SO_2$Alkyl or, $SO_2$Aryl, or joined together to form a 4 to 7 member ring having 0 to 3 heteroatoms;

m is 0 to 5;

n is 0 to 5; and p is 0 to 2.

In another embodiment or the present invention, compounds of Formula 2 are provided:

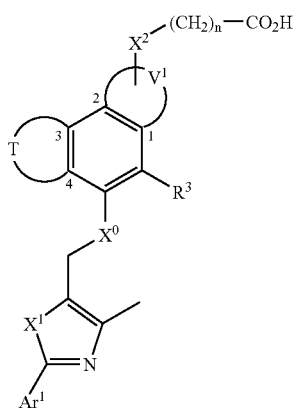

2 or a pharmaceutically acceptable salt thereof, where:

$V^1$ is a saturated or unsaturated, substituted or unsubstituted hydrocarbon chain or hydrocarbon-heteroatom chain having from 3 to 6 atoms wherein the carbon atom of position 1 is connected to the carbon atom of position 2 to form a five to eight member ring where the

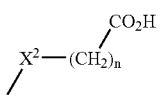

is attached to a substitutionally available position of said ring;

$X^0$ and $X^1$ are independently O or S;

$X^2$ is absent, O, S, or $NR^4$;

$Ar^1$ is substituted or unsubstituted aryl or heteroaryl;

$R^1$, $R^2$, and $R^3$ are independently hydrogen, lower alkyl, lower alkoxy, lower thioalkoxy, $-O(CH_2)_pCF_3$, halogen, nitro, cyano, $-OH$, $-SH$, $-CF_3$, $S(O)_p$Alkyl, $S(O)_p$Aryl, $-(CH_2)_mOR^4$, or $-(CH_2)_mNR^5R^6$, $COR^4$, $-CO_2H$, $-CO_2R^4$, or $-NR^5R^6$ or $R^1$ and $R^2$ are joined together to form a substituted or unsubstituted, saturated or unsaturated cyloalkyl or heterocycloalkyl ring;

$R^4$ is hydrogen, alkyl, alkenyl, alkynyl, or aryl;

$R^5$ and $R^6$ are independently hydrogen, alkyl, alkenyl, alkynyl, cycloalkyl, $SO_2$Alkyl or, $SO_2$Aryl, or joined together to form a 4 to 7 member ring having 0 to 3 heteroatoms;

m is 0 to 5;

n is 0 to 5;

p is 0 to 2; and where T is a saturated or unsaturated, substituted or unsubstituted hydrocarbon chain or hydrocarbon-heteroatom chain having from 2 to 6 atoms wherein the carbon atom of position 3 is connected to the carbon atom of position 4 to form a four to eight member ring.

In another embodiment of the present invention a pharmaceutical composition comprising a compound of Formula 1 and one or more pharmaceutically acceptable carriers, diluents, or excipients is provided.

In one embodiment of the present invention a method of treating, preventing or controlling hypercholesteremia in a mammal is provided. The method comprises administering to the mammal in need thereof a therapeutically effective amount of the compounds of the present invention.

In another embodiment of the present invention a method for treating, preventing, or controlling obesity is provided.

In another embodiment of the present invention a method for treating, preventing, or controlling hyperglycemia is provided.

In another embodiment of the present invention a method for treating, preventing, or controlling hyperlipidemia is provided.

In another embodiment of the present invention a method for treating, preventing, or controlling atherosclerosis is provided.

In another embodiment of the present invention a method for treating, preventing, or controlling hypertriglyceridemia is provided.

In another embodiment of the present invention a method for treating, preventing, or controlling hyperinsulinemia is provided.

In another embodiment of the present invention a method for treating, preventing, or controlling non-insulin dependent diabetes mellitus is provided.

In another embodiment of the present invention a method for treating a patient exhibiting glucose disorders associated with circulating glucocorticoids, growth hormone, catecholamines, glucagon, or parathyroid hormone is provided.

For each disease state treatable, preventable, or controllable by the method of the present invention, a therapeutically effective amount of the compounds of the present invention are administered to the mammal in need thereof.

In yet another embodiment of the present invention, a method of preparing the compounds of the present invention is provided.

DETAILED DESCRIPTION OF THE INVENTION

The following definitions are used, unless otherwise described: alkyl, alkoxy, alkenyl, alkynyl, etc. denote both straight and branched groups; but reference to an individual radical such as "propyl" embraces only the straight chain radical, a branched chain isomer such as "isopropyl" being specifically referred to.

The term "alkyl" as used herein refers to a straight or branched hydrocarbon of from 1 to 11 carbon atoms and includes, for example, methyl, ethyl, n-propyl, isopropyl, n-butyl, sec-butyl, isobutyl, tert-butyl, n-pentyl, n-hexyl, and the like. The alkyl group can also be substituted with one or more of the substituents selected from lower alkoxy, lower thioalkoxy, —O(CH$_2$)$_{0-2}$CF$_3$, halogen, nitro, cyano, =O, =S, —OH, —SH, —CF$_3$, —CO$_2$H, —CO$_2$C$_1$–C$_6$ alkyl, —NH$_2$, —NHC$_1$–C$_6$ alkyl, —CONR'R", or —N(C$_1$–C$_6$alkyl)$_2$ where R' and R" are independently alkyl, akenyl, alkynyl, aryl, or joined together to form a 4 to 7 member ring. Useful alkyl groups have from 1 to 6 carbon atoms (C$_1$–C$_6$ alkyl).

The term "lower alkyl" as used herein refers to a subset of alkyl which means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like. Optionally, lower alkyl is referred to as "C$_1$–C$_6$alkyl."

The term "alkenyl" means a straight or branched unsaturated hydrocarbon radical having from 2 to 12 carbon atoms and includes, for example, ethenyl, 1-propenyl, 2-propenyl, 1-butenyl, 2-butenyl, 1-pentenyl, 2-pentenyl, 3-methyl-3-butenyl, 1-hexenyl, 2-hexenyl, 3-hexenyl, 3-heptenyl, 1-octenyl, 1-nonenyl, 1-decenyl, 1-undecenyl, 1-dodecenyl, and the like.

The term "alkynyl" means a straight or branched hydrocarbon radical having of 2 to 12 carbon atoms having at least one triple bond and includes, for example, 3-propynyl, 1-butynyl, 3-butynyl, 1-pentynyl, 3-pentynyl, 3-methyl-3-butynyl, 1-hexynyl, 3-hexynyl, 3-hexynyl, 3-heptynyl, 1-octynyl, 1-nonynyl, 1-decynyl, 1-undecynyl, 1-dodecynyl, and the like.

The term "alkylene" as used herein refers to a divalent group derived from a straight or branched chain saturated hydrocarbon having from 1 to 10 carbon atoms by the removal of two hydrogen atoms, for example methylene, 1,2-ethylene, 1,1-ethylene, 1,3-propylene, 2,2-dimethylpropylene, and the like. The alkylene groups of this invention can be optionally substituted. The alkylene group can also be substituted with one or more of the substituents selected from lower alkyl, lower alkoxy, lower thioalkoxy, —O(CH$_2$)$_{0-2}$CF$_3$, halogen, nitro, cyano, =O, =S, —OH, —SH, —CF$_3$, —CO$_2$H, —CO$_2$C$_1$–C$_6$ alkyl, —NH$_2$, —NHC$_1$–C$_6$ alkyl, —CONR'R", or —N(C$_1$–C$_6$alkyl)$_2$ where R' and R" are independently alkyl, akenyl, alkynyl, aryl, or joined together to form a 4 to 7 member ring. Useful alkylene groups have from 1 to 6 carbon atoms (C$_1$–C$_6$ alkylene).

The term "halogen" includes chlorine, fluorine, bromine, and iodine.

The term "heteroatom" as used herein represents oxygen, nitrogen, or sulfur (O, N, or S) as well as sulfoxyl or sulfonyl (SO or SO$_2$) unless otherwise indicated.

The term "hydrocarbon chain" as used herein refers to a straight hydrocarbon of from 2 to 6 carbon atoms. The hydrocarbon chain is optionally substituted with one or more substituents selected from lower alkyl, lower alkoxy, lower thioalkoxy, —O(CH$_2$)$_{0-2}$CF$_3$, halogen, nitro, cyano, =O, =S, —OH, —SH, —CF$_3$, —CO$_2$H, —CO$_2$C$_1$–C$_6$ alkyl, —NH$_2$, —NHC$_1$–C$_6$alkyl, —CONR'R", or —N(C$_1$–C$_6$alkyl)$_2$ where R' and R" are independently alkyl, akenyl, alkynyl, aryl, or joined together to form a 4 to 7 member ring.

The term "hydrocarbon-heteroatom chain" as used herein refers to a hydrocarbon chain wherein one or more carbon atoms are replaced with a heteroatom. The hydrocarbon-heteroatom chain is optionally substituted with one or more substituents selected from lower alkyl, lower alkoxy, lower thioalkoxy, —O(CH$_2$)$_{0-2}$CF$_3$, halogen, nitro, cyano, =O, =S, —OH, —SH, —CF$_3$, —CO$_2$H, —CO$_2$C$_1$–C$_6$ alkyl, —NH$_2$, —NH(C$_1$–C$_6$alkyl, —CONR'R", or —N(C$_1$–C$_6$alkyl)$_2$ where R' and R" are independently alkyl, akenyl alkynyl, aryl, or joined together to form a 4 to 7 member ring.

The term "heteroalkylene" as used herein, refers to an alkylene radical as defined above that includes one or more heteroatoms such as oxygen, sulfur, or nitrogen (with valence completed by hydrogen or oxygen) in the carbon chain or terminating the carbon chain.

The terms "lower alkoxy" and "lower thioalkoxy" as used herein refers to O-alkyl or S-alkyl of from 1 to 6 carbon atoms as defined above for "lower alkyl."

The term "aryl" as used herein refers to an aromatic ring which is unsubstituted or optionally substituted by 1 to 4 substituents selected from lower alkyl, lower alkoxy, lower thioalkoxy, —O(CH$_2$)$_p$CF$_3$, halogen, nitro, cyano —OH, —SH, —CF$_3$, —CO$_2$H, —CO$_2$C$_1$–C$_6$ alkyl, —NH$_2$, —NHC$_1$–C$_6$ alkyl, —SO$_2$alkyl, —SO$_2$NH$_2$, —CONR'R", or —N(C$_1$–C$_6$alkyl)$_2$ where R' and R" are independently alkyl, akenyl, alkynyl, aryl, or joined together to form a 4 to 7 member ring. Examples include, but are not limited to phenyl, 2-chlorophenyl, 3-chlorophenyl, 4-chlorophenyl, 2-methylphenyl, 3-methylphenyl, 4-methylphenyl, 2-methoxyphenyl, 3-methoxyphenyl, 4-methoxyphenyl, 2-chloro-3-methylphenyl, 2-chloro-4-methylphenyl, 2-chloro-5-methylphenyl, 3-chloro-2-methylphenyl, 3-chloro-4-methylphenyl, 4-chloro-2-methylphenyl, 4-chloro-3-methylphenyl, 5-chloro-2-methylphenyl, 2,3-dichlorophenyl, 2,5-dichlorophenyl, 3,4-dichlorophenyl, 2,3-dimethylphenyl, 3,4-dimethylphenyl, or the like.

The term "heteroaryl" means an aromatic ring containing one or more heteroatoms. The heteroaryl is optionally substituted with one or more groups enumerated for aryl. Examples of heteroaryl include, but are not limited to thienyl, furanyl, pyrrolyl, pyridyl, pyrimidyl, imidazoyl, pyrazinyl, oxazolyl, thiazolyl, benzothienyl, benzofuranyl, indolyl, quinolinyl, isoquinolinyl, and quinazolinyl, and the like.

The term "heterocycle" means a saturated or unsaturated mono- or polycyclic (i.e. bicyclic) ring incorporating one or more (i.e. 1–4) heteroatoms selected from N, O, and S. It is understood that a heterocycle is optionally substituted with —OH, —O(alkyl), SH, S(alkyl), amine, halogen, acid, ester, amide, amidine, alkyl ketone, aldehyde, nitrile, fluoroalkyl, nitro, sulphone, sulfoxide or C1–6 alkyl. Examples of suitable monocyclic heterocycles include, but are not limited to substituted or unsubstituted thienyl, furanyl, pyrrolyl, imidazolyl, pyrazolyl, thiazolyl, isothiazolyl, oxazolyl, isoxazolyl, triazoiyl, tetrazolyl, pyridinyl, pyrazinyl, pyrimidinyl, piperidinyl, pyrrolidinyl, piperazinyl, azetidinyl, aziridinyl, morpholinyl, thietanyl, oxetaryl. Examples of monocyclic diheterocycles include, but are not limited to, 1-, 2-, 4-, or 5-imidazolyl, 1-, 3-, 4-, or 5-pyrasolyl, 2-, 4-, or 5-thiazolyl, 3-, 4-, or 5-isothiazolyl, 2-, 4-, or 5-oxazolyl, 3-, 4-, or 5-isoxazolyl, 1,3-, or 5-triazolyl, 1-, 2-, or 3-tetrazolyl, 2-pyrazinyl, 2-, 4-, or 5-pyrimidinyl, 1- or 2-piperazinyl, 2-, 3-, or 4-morpholinyl. Examples of suitable bicyclic heterocycles include, but are not limited to indolizinyl, isoindolyl, benzofuranyl, benzothienyl, benzoxazolyl, benzimidazolyl, quinolinyl, isoquinolinyl, quinazolinyl, 1-, 2-, 3-, 4-, 5-, 6-, or 7-indolyl, 1-, 2-, 3-, 5-, 6-, 7-, or 8-indolizinyl, 1-, 2-, 3-, 4-, 5-, 6-, or 7-isoindolyl, 2-, benzimidazolyl, 2-, 4-, 5-, 6-, or 7-benzoxazolyl, 1-, 2-, 4-, 5-, 6-, or 7-benzimidazolyl, 2-, 3-, 4-, 5-, 6-, 7-, or 8-quinolinyl, and 1-, 3-, 4-, 5-, 6-, 7- or 8-isoquinolinyl.

The term "heterocycloalkyl" means a nonaromatic ring with from 4 to 8 members, with up to 4 heteroatoms for example, N, O, and S. Examples of heterocycloalkyl, include, but are not limited to, 2- or 3-tetrahydrothieno, 2- or 3-tetrahydrofurano, 2- or 3-pyrrolidino, 2-, 4-, or 5-thiazolidino, 2-, 4-, or 5-oxazolidino, 2-, 3-, or 4-piperidino, N-morpholin or N-thiamorpholinyl or tetrahydropyrano.

The term "cycloalkyl" means a saturated hydrocarbon ring, and includes for example, cyclopropyl, cyclobutyl, cyclopentyl, cyclohexyl, cycloheptyl, and cyclooctyl, and the like. The cycloalkyl group can be substituted with 1 to 3 substituents from the group of substituents described above for aryl. Preferrably the cycloalkyl will have from 3 to 8 carbon atoms.

The term "patient" means all mammals including humans. Examples of patients include humans, cows, dogs, cats, goats, sheep, pigs, and rabbits.

A "therapeutically effective amount" is an amount of a compound of the present invention that when administered to a patient ameliorates a symptom of dyslipidemia, non-insulin dependent diabetes mellitus, obesity, hyperglycemia, hypercholesteremia, hyperlipidemia, atherosclerosis, hypertriglyceridemia, or hyperinsulinemia.

The term "a pharmaceutically acceptable salt" refers to the relatively non-toxic, inorganic and organic acid or base addition salts of compounds of the present invention. These salts can be prepared in situ during the final isolation and purification of the compounds or by separately reacting the purified compound in its free form with a suitable organic or inorganic acid or base and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," *J. Pharm. Sci.*, 1977;66: 1–19, which is incorporated herein by reference.) The free base form may be regenerated by contacting the salt form with a base. While the free base may differ from the salt form in terms of physical properties, such as solubility, the salts are equivalent to their respective free bases for the purposes of the present invention.

The present invention provides compounds capable of modulating PPAR activity having Formula 1:

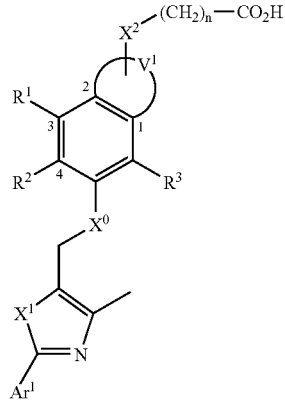

or a pharmaceutically acceptable salt thereof, where:

$V^1$ is a saturated or unsaturated, substituted or unsubstituted hydrocarbon chain or hydrocarbon-heteroatom chain having from 3 to 6 atoms wherein the carbon atom of position 1 is connected to the carbon atom of position 2 to form a five to eight member ring where the

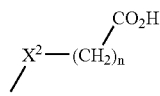

is attached to a substitutionally available position of said ring;

$X^0$ and $X^1$ are independently O or S;

$X^2$ is absent, O, S, or $NR^4$;

$Ar^1$ is substituted or unsubstituted aryl or heteroaryl;

$R^1$, $R^2$, and $R^3$ are independently hydrogen, lower alkyl, lower alkoxy, lower thioalkoxy, $-O(CH_2)_pCF_3$, halogen, nitro, cyano, $-OH$, $-SH$, $-CF_3$, $S(O)_p$Alkyl, $S(O)_p$Aryl, $-(CH_2)_mOR^4$, or $-(CH_2)_mNR^5R^6$, $COR^4$, $-CO_2H$, $-CO_2R^4$, or $-NR^5R^6$ or $R^1$ and $R^2$ are joined together to form a substituted or unsubstituted, saturated or unsaturated cyloalkyl or heterocycloalkyl ring;

$R^4$ is hydrogen, alkyl, alkenyl, alkynyl, or aryl;

$R^5$ and $R^6$ are independently hydrogen, alkyl, alkenyl, alkynyl, cycloalkyl, $SO_2$Alkyl or, $SO_2$Aryl, or joined together to form a 4 to 7 member ring having 0 to 3 heteroatoms;

m is 0 to 5;

n is 0 to 5; and p is 0 to 2.

Additional Examples of compounds of Formula 1 include those where $R^1$, $R^2$, and $R^3$ are independently hydrogen, alkyl, or alkoxy. Examples of compounds of Formula 1 where $R^1$, $R^2$, and $R^3$ are independently alkyl include, but are not limited to, those where $R^1$, $R^2$, and $R^3$ are independently methyl, ethyl, isopropyl, n-propyl, t-butyl, n-butyl, or isobutyl. Examples of compounds of Formula 1 where $R^1$, $R^2$, and $R^3$ are independently alkoxy include, but are not limited to, those where $R^1$, $R^2$, and $R^3$ are independently methoxy, ethoxy, isopropoxy, n-propoxy, t-butoxy, n-butoxy, or isobutoxy.

Additional Examples of compounds of Formula 1 include those where $R^1$ and $R^3$ are hydrogen and $R^2$ is alkyl, or alkoxy. Examples of compounds of Formula 1 where $R^1$ and $R^3$ are hydrogen and $R^2$ is alkyl or alkoxy include, but are not limited to, those where R² is methoxy, ethoxy, isopropoxy, n-propoxy, t-butoxy, n-butoxy, isobutoxy, methyl, ethyl, isopropyl, n-propyl, t-butyl, n-butyl, or isobutyl.

Examples of compounds of Formula 1 include those where V¹ is —CH₂CH₂CO—O—, —CH₂—CH₂—O—CO—, —CH₂—CH₂—CH₂—CH₂—, —HC=CH—HC=CH—, —N=CH—HC=CH—, —HC=N—HC=CH—, —HC=CH—N=CH—, —HC=CH—HC=N—, —CH₂—CH₂—CH₂—, —CH₂—CH₂—O—CH₂—, —CH₂—HC=CH—, —CH₂CH₂—NH—CH₂—, —COCH=CH—O—, —O—CH=CH—CO—, —O—CH=CH—, —CH=CH—O—, —O—CH₂—CH=CH—, —CH=CH—CH₂—O—, —CH₂—CH₂—CO—NR⁴, —CH₂—CH₂—CO—CH₂—, —CH₂—CH₂—NR⁴—CH₂—, —CH₂—NR⁴—CH₂—CH₂—, —CH=CH—NR⁴—, —NR⁴—CH=CH—, —CH=CH—CH₂, —CH₂—CH₂—NR⁴—, —NR⁴—CH₂—CH₂—, —O—CH₂—CH₂—, —O—CH₂—CH₂—CH₂—, —CH₂—CH₂—O—, —CH₂—CH₂—CH₂—O—, —O—CH(CH₃)—CH₂—CH₂—, —CH₂—CH₂—CH(CH₃)—O—, —CH₂—CH₂—CH₂—NR⁴—, —NR⁴—CH₂—CH₂—CH₂—, —CH₂—CH₂—CO—NR⁴, —NR⁴—CO—CH₂—CH₂—, —O—NR⁴—CO—, —CO—NR⁴—O—, —O—CH₂—CH₂—CH₂—, —CH₂—CH₂—CH₂—O—, —CH₂—CH₂—NR⁴—CO—, —CH₂—CH₂—CH₂—CO—, —CO—CH₂—CH₂—CH₂—, —NR4—CO—CH₂—CH₂—, —CO—NR⁴—CH₂—CH₂—, —CH₂—CH₂—CO—, —CH₂—CO—CH₂—, —CH₂=CH₂—S—, —S—CH₂=CH₂=CH₂—, or —CO—CH₂—CH₂—. It will be understood that the left-most atom of these groups in attached to the atom labeled "1" in Formula 1 and the right-most atom of these groups is attached to the atom label "1" in Formula 1.

Furthermore, examples of compounds of Formula 1 include those where V¹ is optionally substituted with 1 or more substituents selected from lower alkyl, lower alkoxy, lower thioalkoxy, —O(CH₂)₀₋₂CF₃, halogen, nitro, cyano, =O, =S, —OH, —SH, —CF₃, —CO₂H, —CO₂C₁-C₆ alkyl, —NH₂, —NHC₁-C₆ alkyl, —CONR'R", or —N(C₁-C₆alkyl)₂ where R' and R" are independently alkyl, akenyl, alkynyl, aryl, or joined together to form a 4 to 7 member ring and —N(C₁-C₆alkyl)₂.

Additional examples of compounds of Formula 1, include but are not limited to, compounds of Formulae 1a–1h:

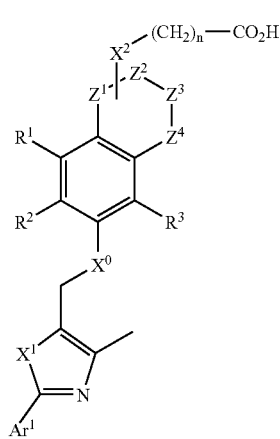

1a

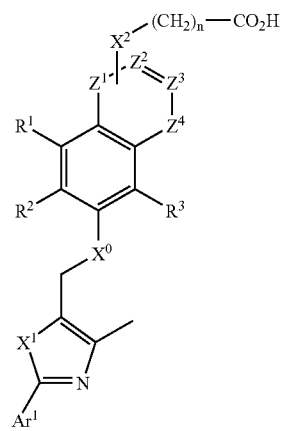

1b

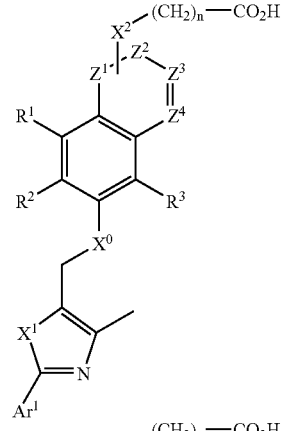

1c

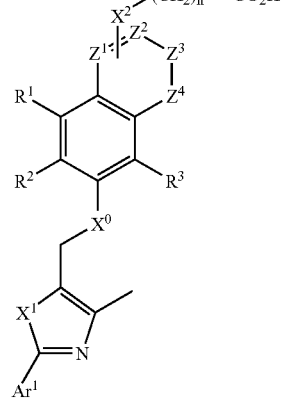

1d

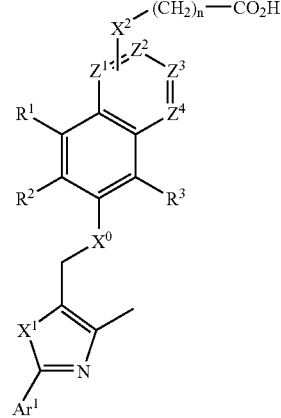

1e

-continued

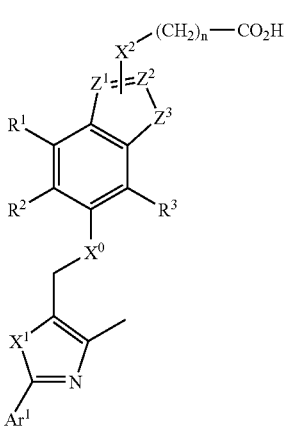

1f

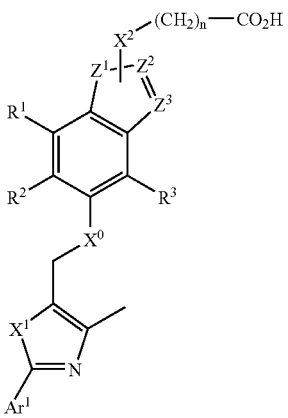

1g

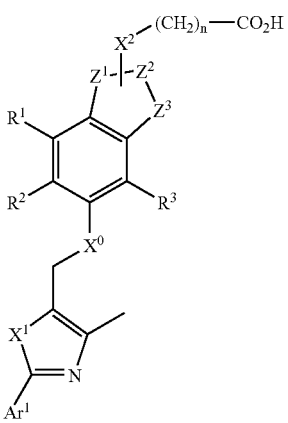

1h or a pharmaceutically acceptable salt thereof, where:

$X^0$ and $X^2$ are independently O or S;

$X^2$ is absent, O, S, or $NR^4$;

$Ar^1$ is substituted or unsubstituted aryl or heteroaryl;

$R^1$, $R^2$, and $R^3$ are independently hydrogen, lower alkyl, lower alkoxy, lower thioalkoxy, —$O(CH_2)_pCF_3$, halogen, nitro, cyano, —OH, —SH, —$CF_3$, $S(O)_p$Alkyl, $S(O)_p$Aryl, —$(CH_2)_mOR^4$, or —$(CH_2)_mNR^5R^6$, $COR^4$, —$CO_2H$, —$CO_2R^4$, or —$NR^5R^6$ or $R^1$ and $R^2$ are joined together to form a substituted or unsubstituted, saturated or unsaturated cyloalkyl or heterocycloalkyl ring;

$R^4$ is hydrogen, alkyl, alkenyl, alkynyl, or aryl;

$R^5$ and $R^6$ are independently hydrogen, alkyl, alkenyl, alkynyl, cycloalkyl, $SO_2$Alkyl or, $SO_2$Aryl, or joined together to form a 4 to 7 member ring having 0 to 3 heteroatoms;

m is 0 to 5;

n is 0 to 5; and p is 0 to 2.

$Z^1$, $Z^2$, $Z^3$, and $Z^4$ are independently O, S, $CR^5R^6$, $NR^4$, or N; and $Z^1$, $Z^2$, $Z^3$, and $Z^4$ are bonded to a sufficient number of hydrogen atoms or substituents to complete the valency of each atom with the proviso that $Z^1$, $Z^2$, $Z^3$, and $Z^4$ are not all heteroatoms and that not more than two adjacent atoms in $Z^1$, $Z^2$, $Z^3$, and $Z^4$ are heteroatoms and that in Formulae 1b, 1c, 1d, 1f, and 1g, $Z^1$, $Z^2$, $Z^3$, and $Z^4$ are not all carbon atoms.

Additional examples of compound of Formula 1 include, but are not limited to, those compounds of Formula.2:

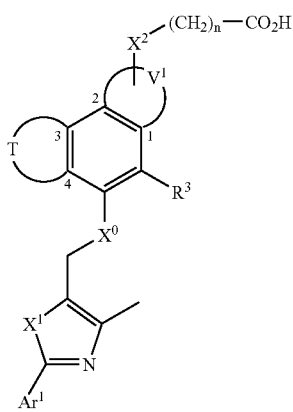

2 or a pharmaceutically acceptable salt thereof, where:

$V^1$ is a saturated or unsaturated, substituted or unsubstituted hydrocarbon chain or hydrocarbon-heteroatom chain having from 3 to 6 atoms wherein the carbon atom of position 1 is connected to the carbon atom of position 2 to form a five to eight member ring where the

is attached to a substitutionally available position of said ring;

$X^0$ and $X^1$ are independently O or S;

$X^2$ is absent, O, S, or $NR^4$;

$Ar^1$ is substituted or unsubstituted aryl or heteroaryl;

$R^1$, $R^2$, and $R^3$ are independently hydrogen, lower alkyl, lower alkoxy, lower thioalkoxy, —$O(CH_2)_pCF_3$, halogen, nitro, cyano, —OH, —SH, —$CF_3$, $S(O)_p$Alkyl, $S(O)_p$Aryl, —$(CH_2)_mOR^4$, or —$(CH_2)_mNR^5R^6$, $COR^4$, —$CO_2H$, —$CO_2R^4$, or —$NR^5R^6$ or $R^1$ and $R^2$ are joined together to form a substituted or unsubstituted, saturated or unsaturated cyloalkyl or heterocycloalkyl ring;

$R^4$ is hydrogen, alkyl, alkenyl, alkynyl, or aryl;

$R^5$ and $R^6$ are independently hydrogen, alkyl, alkenyl, alkynyl, cycloalkyl, $SO_2$Alkyl or, $SO_2$Aryl, or joined together to form a 4 to 7 member ring having 0 to 3 heteroatoms;

m is 0 to 5;

n is 0 to 5;

p is 0 to 2; and where T is a saturated or unsaturated, substituted or unsubstituted hydrocarbon chain or hydrocarbon-heteroatom chain having from 2 to 6 atoms wherein the carbon atom of position 3 is connected to the carbon atom of position 4 to form a four to eight member ring.

Examples of compounds of Formula 1 include those where T is $-CH_2CH_2CO-O-$, $-CH_2-CH_2-O-CO-$, $-CH_2-CH_2-CH_2-CH_2-$, $-HC=CH-HC=CH-$, $-N=CH-HC=CH-$, $-HC=N-HC=CH-$, $-HC=CH-N=CH-$, $-HC=CH-HC=N-$, $-CH_2-CH_2-CH_2-$, $-CH_2-CH_2-O-CH_2$, $-CH_2-HC=CH-$, $-CH_2CH_2-NH-CH_2-$, $-COCH=CH-O-$, $-O-CH=CH-CO-$, $-CH=CH-NR^4-$, $-NR^4-CH=CH-$, $-CH=CH-CH_2-$, $-CH_2-CH_2-NR^4-$, $-NR^4-CH_2-CH_2-$, $-O-CH_2-CH_2-$, $-CH_2-CH_2-O-$, $-CH_2-CH_2-CO-$, $-CH_2-CO-CH_2-$, $-CO-CH_2-CH_2-$, $-CH_2-CH_2-CH_2-CO-$, $-CO-CH_2-CH_2-CH_2-$, $-CH_2-CO-CH_2-CH_2-$, $-CH_2-CH_2-CO-CH_2-$, $-CH_2-CH_2-CH_2-NR^4-$, $-NR^4-NR^4-CH_2-CH_2-CH_2-$, $-O-CH_2-CH_2-CH_2-$, $-CH_2-CH_2-CH_2-O-$, $-CO-NR^4-CH_2-CH_2-$, $NR^4CO-CH_2-CH_2-$, $-CH_2-CH_2-NR^4-CO-$, or $-CH_2-CH_2-CO-NR^4-$. It will be understood that the left-most atom of these groups in attached to the atom labeled "4" in Formula 2 and the right-most atom of these groups is attached to the atom label "3" in Formula 2.

Furthermore, examples of compounds of Formula 1 include those where T is optionally substituted with 1 or more substituents selected from lower alkyl, lower alkoxy, lower thioalkoxy, $-O(CH_2)_{0-2}CF_3$, halogen, nitro, cyano, =O, =S, $-OH$, $-SH$, $-CF_3$, $-CO_2H$, $-CO_2C_1-C_6$ alkyl, $-NH_2$, $-NHC_1-C_6$ alkyl, $-CONR'R''$, or $-N(C_1-C_6alkyl)_2$ where R' and R" are independently alkyl, akenyl, alkynyl, aryl, or joined together to form a 4 to 7 member ring.

Other examples of compounds of Formula 2 include, but are not limited to, those where $V^1$ is:

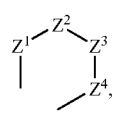
(a)

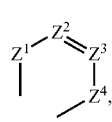
(b)

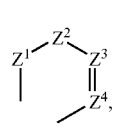
(c)

-continued

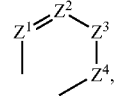
(d)

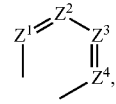
(e)

(f)

(g)

(h)

where:

$Z^1$, $Z^2$, $Z^3$, and $Z^4$ are independently O, S, $CR^5R^6$, $NR^4$, or N; and $Z^1$, $Z^2$, $Z^3$, and $Z^4$ are bonded to a sufficient number of hydrogen atoms or substituents (as defined above for $V^1$) to complete the valency of each atom with the proviso that $Z^1$, $Z^2$, $Z^3$, and $Z^4$ are not all heteroatoms and that not more than two adjacent atoms in $Z^1$, $Z^2$, $Z^3$, and Z are heteroatoms and that in Formulae 2a, 2b, 2c, 2d, 2g and 2h $Z^1$, $Z^2$, $Z^3$, and $Z^4$ are not all carbon atoms. Accordingly, such examples include those of Formulae 2a –2h:

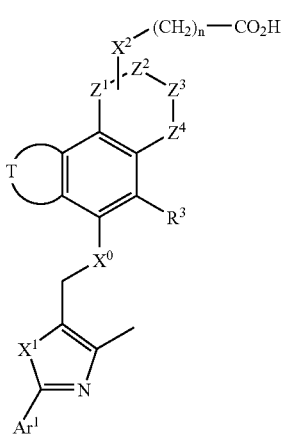
2a

2b
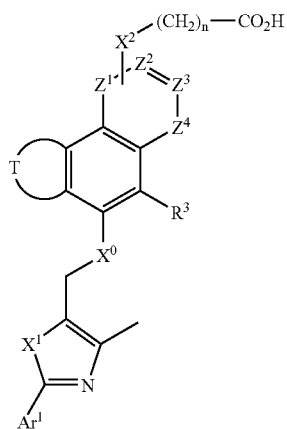
2c
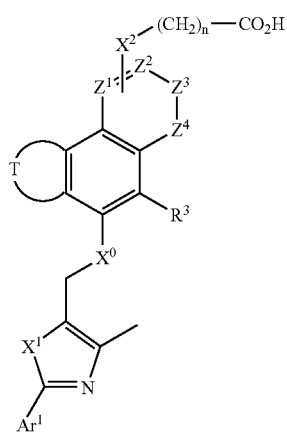
2d
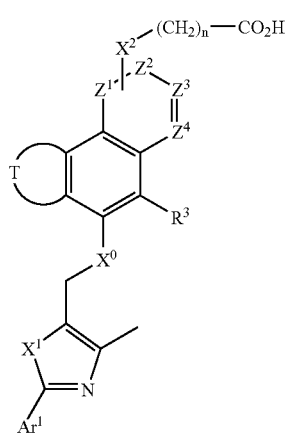
2e
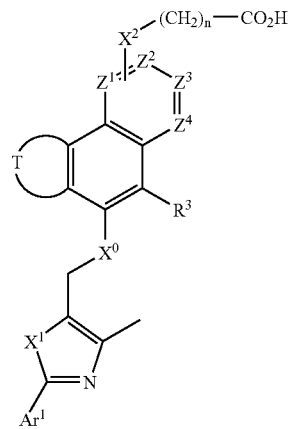
2f
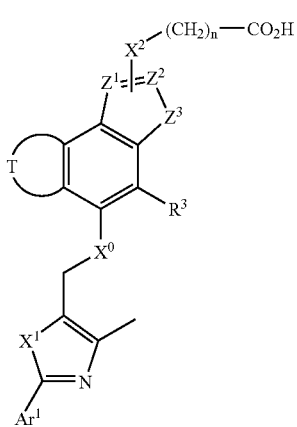
2g
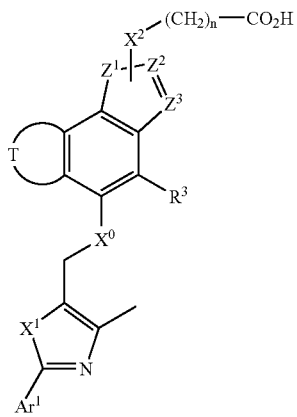

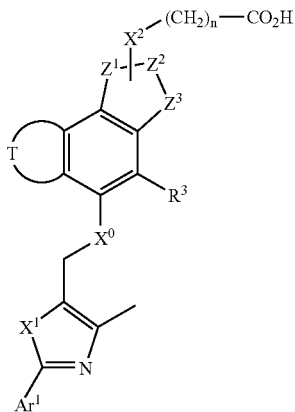

2h or a pharmaceutically acceptable salt thereof, where:

$X^0$ and $X^1$ are independently O or S;

$X^2$ is absent, O, S, or $NR^4$;

$Ar^1$ is substituted or unsubstituted aryl or heteroaryl;

$R^1$, $R^2$, and $R^3$ are independently hydrogen, lower alkyl, lower alkoxy, lower thioalkoxy, —O(CH$_2$)$_p$CF$_3$, halogen, nitro, cyano, —OH, —SH, —CF$_3$, S(O)$_p$Alkyl, S(O)$_p$Aryl, —(CH$_2$)$_m$OR$^4$, or —(CH$_2$)$_m$NR$^5$R$^6$, COR$^4$, —CO$_2$H, —CO$_2$R$^4$, or —NR$^5$R$^6$ or $R^1$ and $R^2$ are joined together to form a substituted or unsubstituted, saturated or unsaturated cyloalkyl or heterocycloalkyl ring;

$R^4$ is hydrogen, alkyl, alkenyl, alkynyl, or aryl;

$R^5$ and $R^6$ are independently hydrogen, alkyl, alkenyl, alkynyl, cycloalkyl, SO$_2$Alkyl or, SO$_2$Aryl, or joined together to form a 4 to 7 member ring having 0 to 3 heteroatoms;

m is 0 to 5;

n is 0 to 5;

p is 0 to 2;

T is a saturated or unsaturated, substituted or unsubstituted hydrocarbon chain or hydrocarbon-heteroatom chain having from 2 to 6 atoms wherein the carbon atom of position 3 is connected to the carbon atom of position 4 to form a four to eight member ring;

$Z^1$, $Z^2$, $Z^3$, and $Z^4$ are independently O, S, CR$^5$R$^6$, NR$^4$, or N; and $Z^1$, $Z^2$, $Z^3$, and $Z^4$ are bonded to a sufficient number of hydrogen atoms or substituents (as defined above for $V^1$) to complete the valency of each atom with the proviso that $Z^1$, $Z^2$, $Z^3$, and $Z^4$ are not all heteroatoms and that not more than two adjacent atoms in $Z^1$, $Z^2$, $Z^3$, and Z are heteroatoms and that in Formulae 2a, 2b, 2c, 2d, 2g and 2h, $Z^1$, $Z^2$, $Z^3$, and $Z^4$ are not all carbon atoms.

Further examples of compounds of Formulae 1 and 2 include, but are not limited to, those where the heteroatom of the hydrocarbon-heteroatom chain is is N, O, or S.

Furthermore, examples of compounds of Formula 2 include those where T is optionally substituted with 1 or more substituents selected from lower alkyl, lower alkoxy, lower thioalkoxy, —O(CH$_2$)$_{0-2}$CF$_3$, halogen, nitro, cyano, =O, =S, —OH, —SH, —CF$_3$, —CO$_2$H, —CO$_2$C$_1$–C$_6$ alkyl, —NH$_2$, —NHC$_1$–C$_6$ alkyl, —CONR'R", or —N(C$_1$–C$_6$alkyl)$_2$ where R' and R" are independently alkyl, akenyl, alkynyl, aryl, or joined together to form a 4 to 7 member ring.

Examples of compounds of Formula 1 include

5-[4-Methyl-2-(4-trifluoromethyl-phenyl)-thiazol-5-ylmethylsulfanyl]-indan-2-carboxylic acid;

{5-[4-Methyl-2-(4-trifluoromethyl-phenyl)-thiazol-5-ylmethylsulfanyl]-indan-2-yl}-acetic acid;

6-[4-Methyl-2-(4-trifluoromethyl-phenyl)-thiazol-5-ylmethylsulfanyl]-1-benzopyran-2-carboxylic acid;

{5-[4-Methyl-2-(4-trifluoromethyl-phenyl)-thiazol-5-ylmethylsulfanyl]-2,3-dihydro-benzofuran-2-yl}-acetic acid;

{6-[4-Methyl-2-(4-trifluoromethyl-phenyl)-thiazol-5-ylmethylsulfanyl]-1-benzopyran-2-yl}-acetic acid;

5-[4-Methyl-2-(4-trifluoromethyl-phenyl)-thiazol-5-ylmethylsulfanyl]-benzofuran-2-carboxylic acid;

{6-[4-Methyl-2-(4-trifluoromethylphenyl)thiazol-5-ylmethylsulfanyl]-1-oxo-3,4-dihydro-1H-naphthalen-2-yl}acetic acid;

{2-Methyl-6-[4-methyl-2-(4-trifluoromethyl-phenyl)-thiazol-5-ylmethylsulfanyl]-chroman-2-yl}-acetic acid;

{2,8-Dimethyl-6-[4-methyl-2-(4-trifluoromethyl-phenyl)-thiazol-5-ylmethylsulfanyl]-chroman-2-yl}-acetic acid;

{6-[4-Methyl-2-(4-trifluoromethyl-phenyl)-thiazol-5-ylmethylsulfanyl]-3,4-dihydro-1H-isoquinolin-2-yl}-acetic acid;

{6-[4-Methyl-2-(4-trifluoromethyl-phenyl)-thiazol-5-ylmethylsulfanyl]-3,4-dihydro-2H-quinolin-1-yl}-acetic acid;

{6-[4-Methyl-2-(4-trifluoromethyl-phenyl)-thiazol-5-ylmethylsulfanyl]-2-oxo-3,4-dihydro-2H-dihydro-2H-isoquinolin-1-yl}-acetic acid;

7-Methoxy-6-[4-methyl-2-(4-trifluoromethyl-phenyl)-thiazol-5-ylmethylsulfanyl]-1,2,3,4-tetrahydro-naphthalen-2-yl}-acetic acid;

7-Methoxy-6-[4-methyl-2-(4-trifluoromethyl-pheny)-thiazol-5-ylmethylsulfanyl]-chroman-2-yl-acetic acid;

7-Methyl-6-[4-methyl-2-(4-trifluoromethyl-pheny)-thiazol-5-ylmethylsulfanyl]-chroman-2-yl-acetic acid;

6-[4-Methyl-2-(4-trifluoromethyl-pheny)-thiazol-5-ylmethylsulfanyl]-2H-chromene-3-carboxylic acid;

6-[4-Methyl-2-(4-trifluoromethyl-pheny)-thiazol-5-ylmethylsulfanyl]-chroman-3-carboxylic acid;

6-[4-Methyl-2-(4-trifluoromethyl-pheny)-thiazol-5-ylmethylsulfanyl]-chroman-3-yl-acetic acid;

{6-Methoxy-5-[4-methyl-2-(4-trifluoromethyl-phenyl)-thiazol-5-ylmethylsulfanyl]-indan-1-yl}-acetic acid;

6-[4-Methyl-2-(4-trifluoromethyl-pheny)-thiazol-5-ylmethylsulfanyl]-4-oxo-chroman-3-ylidene-acetic acid;

3-{5-[4-Methyl-2-(4-trifluoromethyl-pheny)-thiazol-5-ylmethylsulfanyl]-2,3-dihydro-indol-1-yl }-propionic acid;

6-Methoxy-5-[4-Methyl-2-(4-trifluoromethyl-pheny)-thiazol-5-ylmethylsulfanyl]-3-oxo-3H-benzo[d]isoxazo-2-yl-acetic acid;

{5-[4-Methyl-2-(4-trifluoromethyl-phenyl)-thiazol-5-yl-methylsulfanyl]-indol-1-yl}-acetic acid; and pharmaceutically acceptable salts thereof.

Further examples of compounds of Formula 1 include

{6-[4-Methyl-2-(4-trifluoromethyl-phenyl)-thiazol-5-ylmethylsulfanyl]-chroman-2-yl}-acetic acid, (2S);

{6-[4-Methyl-2-(4-trifluoromethyl-phenyl)-thiazol-5-ylmethylsulfanyl]-chroman-2-yl}-acetic acid, (2R);

{5-[4-Methyl-2-(4-trifluoromethyl-phenyl)-thiazol-5-ylmethylsulfanyl]-2,3-dihydro-benzofuran-2-yl}-acetic acid, (2R);

{5-[4-Methyl-2-(4-trifluoromethyl-phenyl)-thiazol-5-ylmethylsulfanyl]-2,3-dihydro-benzofuran-2-}-acetic acid, (2S);

6-[4-Methyl-2-(4-trifluoromethyl-phenyl)-thiazol-5-yl-methylsulfanyl]-chroman-2-carboxylic acid, (2S);

6-[4-Methyl-2-(4-trifluoromethyl-phenyl)-thiazol-5-ylmethylsulfanyl]-chroman-2-carboxylic acid, (2R);

2-Methyl-6-[4-methyl-2-(4-trifluoromethyl-phenyl)-thiazol-5-ylmethylsulfanyl]-chroman-2-carboxylic acid, (2R);

2-Methyl-6-[4-methyl-2-(4-trifluoromethyl-phenyl)-thiazol-5-ylmethylsulfanyl]-chroman-2-carboxylic acid, (2S);

{7-[4-Methyl-2-(4-trifluoromethyl-phenyl)-thiazol-5-ylmethylsulfanyl]-2,3,4,5-tetrahydro-benzo[b]oxepin-2-yl}-acetic acid, (2S);

{7-[4-Methyl-2-(4-trifluoromethyl-phenyl)-thiazol-5-ylmethylsulfanyl]-2,3,4,5-tetrahydro-benzo[b]oxepin-2-yl}-acetic acid, (2R); and pharmaceutically acceptable salts thereof.

Yet further examples of compounds of Formula 1 include
{4-Methyl-5-[4-methyl-2-(4-trifluoromethyl-phenyl)-thiazol-5-ylmethoxy]-indol-1-yl}-acetic acid;

{2-Methyl-5-[4-methyl-2-(4-trifluoromethyl-phenyl)-thiazol-5-ylmethoxy]-indol-1-yl}-acetic acid;

{3-Methyl-5-[4-methyl-2-(4-trifluoromethyl-phenyl)-thiazol-5-ylmethoxy]-indol-1-yl}-acetic acid;

{6-Methoxy-5-[4-methyl-2-(4-trifluoromethyl-phenyl)-thiazol-5-ylmethoxy]-indol-1-yl}-acetic acid;

1-Carboxymethyl-2-methyl-5-[4-methyl-2-(4-trifluoromethyl-phenyl)-thiazol-5-ylmethoxy]-1H-indole-3-carboxylic acid ethyl ester;

{6-[4-Methyl-2-(4-trifluoromethyl-phenyl)-thiazol-5-yl-methoxy]-1H-indol-3-yl}-acetic acid;

{1-Methyl-6-[4-methyl-2-(4-trifluoromethyl-phenyl)-thiazol-5-ylmethoxy]-1H-indol-3-yl}-acetic acid;

{5-Methoxy-1-methyl-6-[4-methyl-2-(4-trifluoromethyl-phenyl)-thiazol-5-ylmethylsulfanyl]-1H-indol-3-yl}-acetic acid;

{5-Methoxy-6-[4-methyl-2-(4-trifluoromethyl-phenyl)-thiazol-5-ylmethylsulfanyl]-1H-indol-3-yl}-acetic acid; and pharmaceutically acceptable salts thereof.

Yet further examples of compounds of Formula 1 include
{5-[4-Methyl-2-(4-trifluoromethyl-phenyl)-thiazol-5-yl-methoxy]-indol-1-yl}-acetic acid;

{6-[4-methyl-2-(4-trifluoromethyl-phenyl)-thiazol-5-yl-methoxy]-benzo[b]thiophen-3-yl}-acetic acid; and pharmaceutically acceptable salts thereof.

Certain of the compounds of the present invention possess one or more chiral centers and each center may exist in the R or S configuration. The present invention includes all diastereomeric, enantiomeric, and epimeric forms as well as the appropriate mixtures thereof. Stereoisomers may be obtained, if desired, by methods known in the art as, for example, the separation of stereoisomers by chiral chromatographic columns. Additionally, the compounds of the present invention may exist as geometric isomers. The present invention includes all cis, trans, syn, anti, entgegen (E), and zusammen (Z) isomers as well as the appropriate mixtures thereof.

In some situations, compounds may exist as tautomers. All tautomers are included within Formula 1 and are provided by this invention.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The present invention includes all pharmaceutically acceptable, non-toxic esters of the compounds of Formula 1. Such esters include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

The compounds of the present invention are suitable to be administered to a patient for the treatment, control, or prevention of non-insulin dependent diabetes mellitus, hypercholesteremia, hyperlipidemia, obesity, hyperglycemia, hyperlipidemia, atherosclerosis, hypertriglyceridemia, and hyperinsulinemia. Accordingly, the compounds of the present invention can be administered to a patient alone or as part of a composition that contains other components such as excipients, diluents, and carriers, all of which are well-known in the art. The compositions can be administered to humans and animals either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 2,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depend on a numbers of factors including the requirements of the patient, the severity of the condition being treated, and the pharmacological activity of the compound being used. The determination of optimum dosages for a particular patient is well-known to those skilled in the art.

PREPARATION OF COMPOUNDS OF THE INVENTION

The present invention contains compounds that can be synthesized in a number of ways familiar to one skilled in organic synthesis. The compounds outlined herein can be synthesized according to the methods described below, along with methods typically utilized by a synthetic chemist, and combinations or variations of those methods which are generally known to one skilled in the art of synthetic chemistry. The synthetic route of compounds in the present invention is not limited to the methods outlined below. It is assumed one skilled in the art will be able to use the schemes outlined below to synthesize compounds claimed in this invention. Individual compounds may require manipulation of the conditions in order to accommodate various functional groups. A variety of protecting groups generally known to one skilled in the art may be required. Purification, if necessary, can be accomplished on a silica gel column eluted with the appropriate organic solvent system. Also, reverse phase HPLC or recrystallization may be employed as needed.

In still another embodiment of the present invention, a method of preparing the compounds of the present invention is provided. The method of the present invention comprises reaction of a compound having Formula:

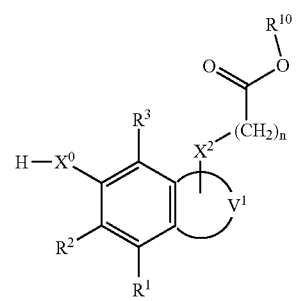

in a solvent in the presence of a base such as cesium carbonate with:

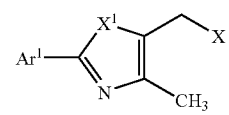

wherein
$V^1$, $R^1$, $R^2$, $R^3$, $R^4$, $R^5$, $R^6$, $X^0$, $X^1$, $X^2$, $Ar^1$, m, n, and p are the same as described above;
X is a halogen; and
$R^{10}$ is a lower alkyl.

The resulting ester is then converted to the compounds of Formulae 1 and 2 by various methods know in the art for the conversion of esters to acids, such as via hydrolysis for example. A useful aryl halide, for example, is 5-chloromethyl-4-methyl-2-(4-trifluoromethyl-phenyl)-thiazole. Compounds 1, 1a–e, 2, 2a–e, and 3–53 will be provided when T and $V^1$ are defined as given above.

The compounds of the present invention can be prepared using the synthetic route outlined in Scheme 1. With reference to Scheme 1, compound A is converted to the ester B. Although any compatible method for esterification may be used, a useful method is to react compound A with an alcohol, such as methanol, in the presence of an acid such as hydrochloric acid. Ester B is then reacted with cholorsulfonic acid to form compound C. Compound C is then reduced to form compound D. Compound D is then alkylated with the halide compound E to form compound F. A useful halide compound E is 5-chloromethyl-4-methyl-2-(4-trifluoromethyl-phenyl)-thiazole, for example. Compound F is then saponified with aqueous LiOH in the THF to give the final compound G. $Ar^1$, $X^0$, $X^1$, $R^1$, $R^2$, $R^3$, and $R^4$ are the same as defined above for Formulas 1–2 above; X is a halogen. Compound G corresponds to the compounds described by Formula 1–2 above when $X^0$ is S. Specifically, compound G corresponds to Formula 2 when $R^1$ and $R^2$ are joined together to form a ring.

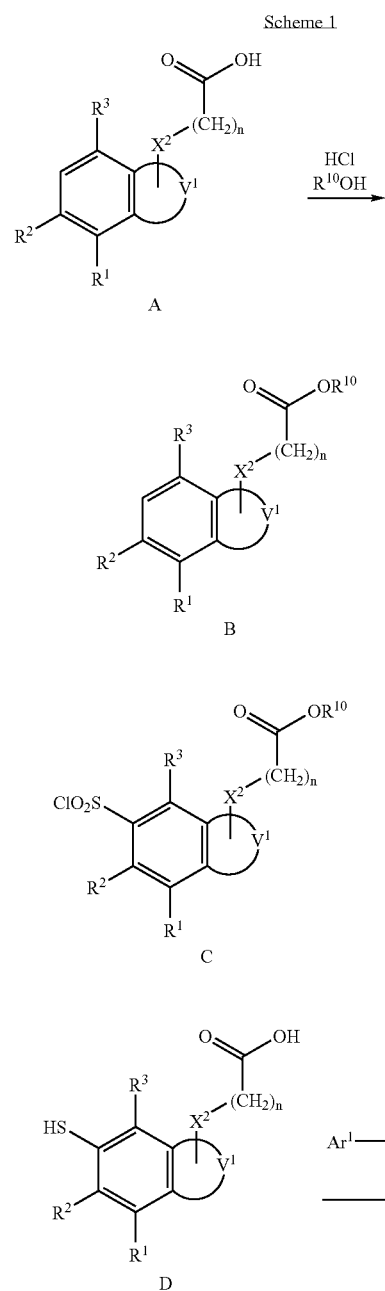

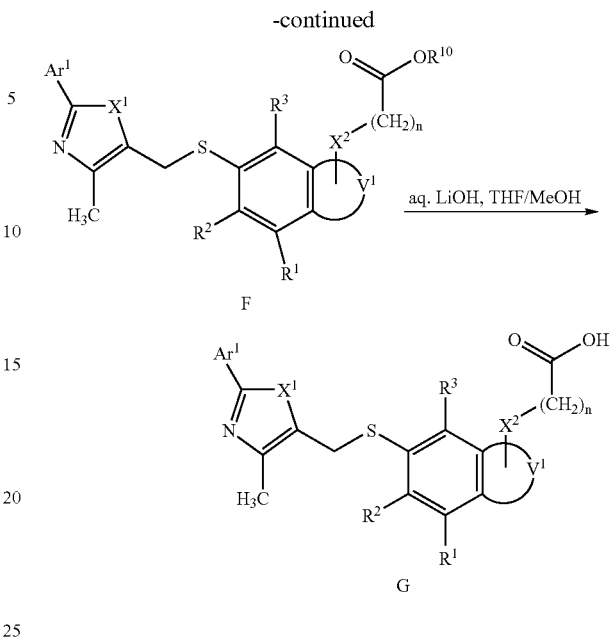

Alternatively, the compounds of the present invention can be prepared using the synthetic route outlined in Scheme 2. With reference to Scheme 2, compound H is reacted with a reducing agent such a Dibal to form compounds with formula I. Compound I is then reacted with dimethyl malonate to form compounds with formula J. Compounds with formula J is then reacted with cholorsulfonic acid followed by a reduction to form compound K. Compound K is then alkylated with the halide compound E. The resulting compound is then reacted with acid to form compound L. A useful halide compound E is 5-chloromethyl-4-methyl-2-(4-trifluoromethyl-phenyl)-thiazole, for example. Compound L corresponds to the compounds described by Formula 1–2 above when $V^1$ is —CH2-CH2-CH—O—, $X^0$ is S, and n is 1. Specifically, compound L corresponds to Formula 2 when $R^1$ and $R^2$ are joined together to form a ring, $V^1$ is —CH2-CH2-CH—O— and n is 1.

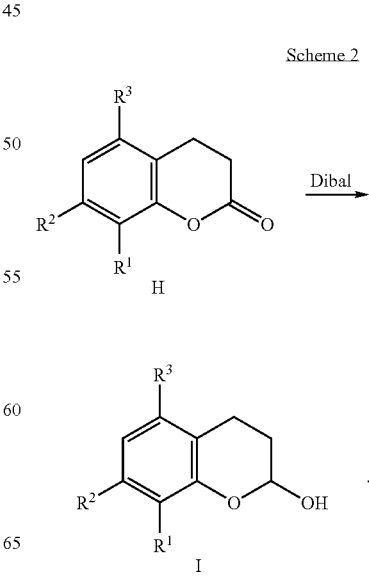

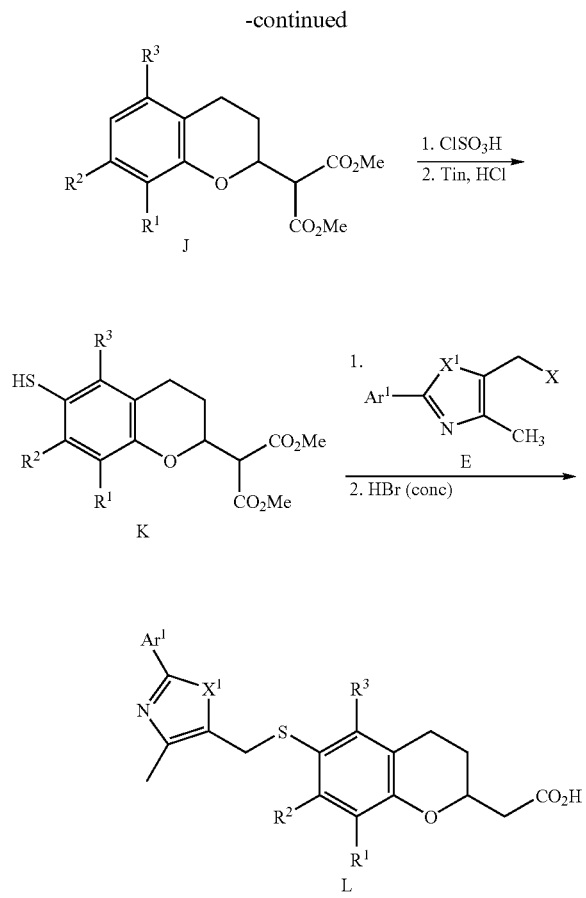

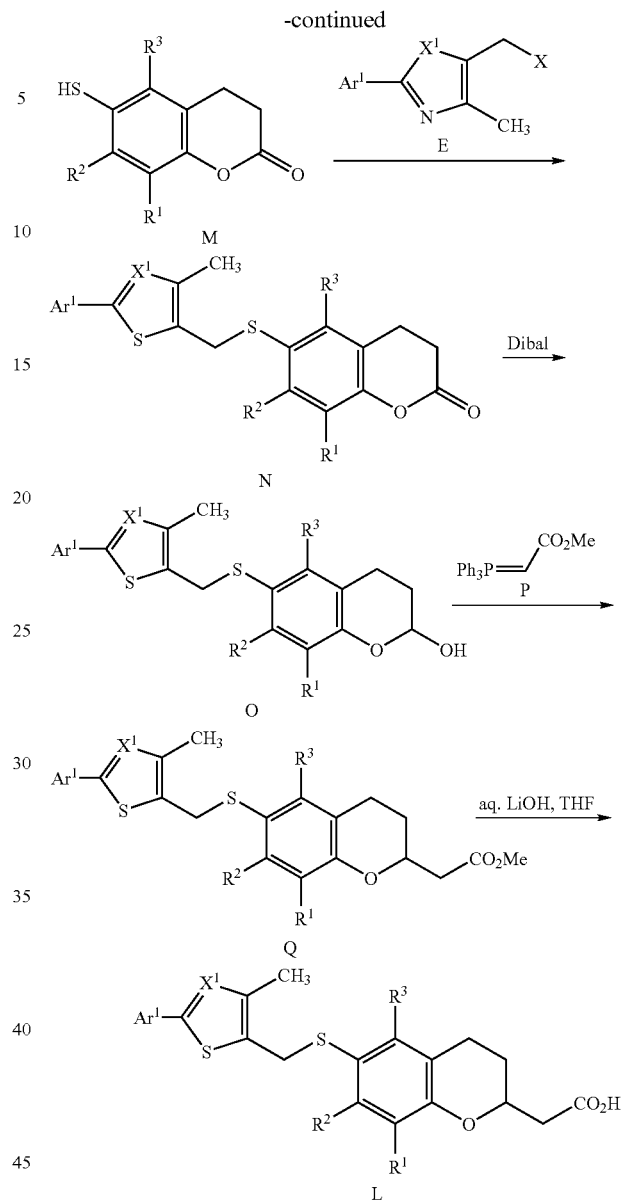

Scheme 3 provide yet another synthetic route to the compounds of the present invention. Compound H is reacted with cholorsulfonic acid followed by reduction to form compound M. Compound M is then alkylated with the halide compound E to form compound N. A useful halide compound E is 5-chloromethyl-4-methyl-2-(4-trifluoromethyl-phenyl)-thiazole, for example. Compound N is reacted with a reducing agent such as Dibal to form compounds with formula O. Compound O s reacted with Wittig reagent P to form compound Q. Compound Q is then saponified with aqueous LiOH to form compound L. W, Y, $Ar^1$, $X^0$, $X^1$, $R^1$, $R^2$, $R^3$, and $R^4$ are the same as defined above for Formulas 1–2 above; X is a halogen. Compound L corresponds to the compounds described by Formula 1–2 above when $X^0$ is S. Specifically, compound L corresponds to Formula 2 when $R^1$ and $R^2$ are joined together to form a ring.

Scheme 3

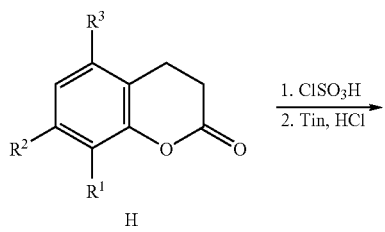

Another alternative synthetic route to the compounds of the present invention is provided in Scheme 4. Compound R may be prepared by de-methylation of the corresponding methyl ether with boron tribromide. Compound S is prepared by thiocarbamoylation of compound R. Compound T is then prepared by a Newman-Karnes rearrangement of compound S in refluxing diphenyl ether. Saponification and re-esterification of compound S then gives compound D. Compound D is then alkylated with the halide compound E to form compound F. A useful halide compound E is 5-chloromethyl-4-methyl-2-(4-trifluoromethyl-phenyl)-thiazole, for example. Compound F is then saponified with aqueous LiOH in the THF to give the final compound G. $R^1$, $R^2$, $R^3$, and $R^4$ are the same as defined above for Formulas I–IV above; X is a halogen. Compound G corresponds to the compounds described by Formula 1–2 above. Specifically, compound G corresponds to Formula 2 when $R^1$ and $R^2$ are joined together to form a ring.

Scheme 4

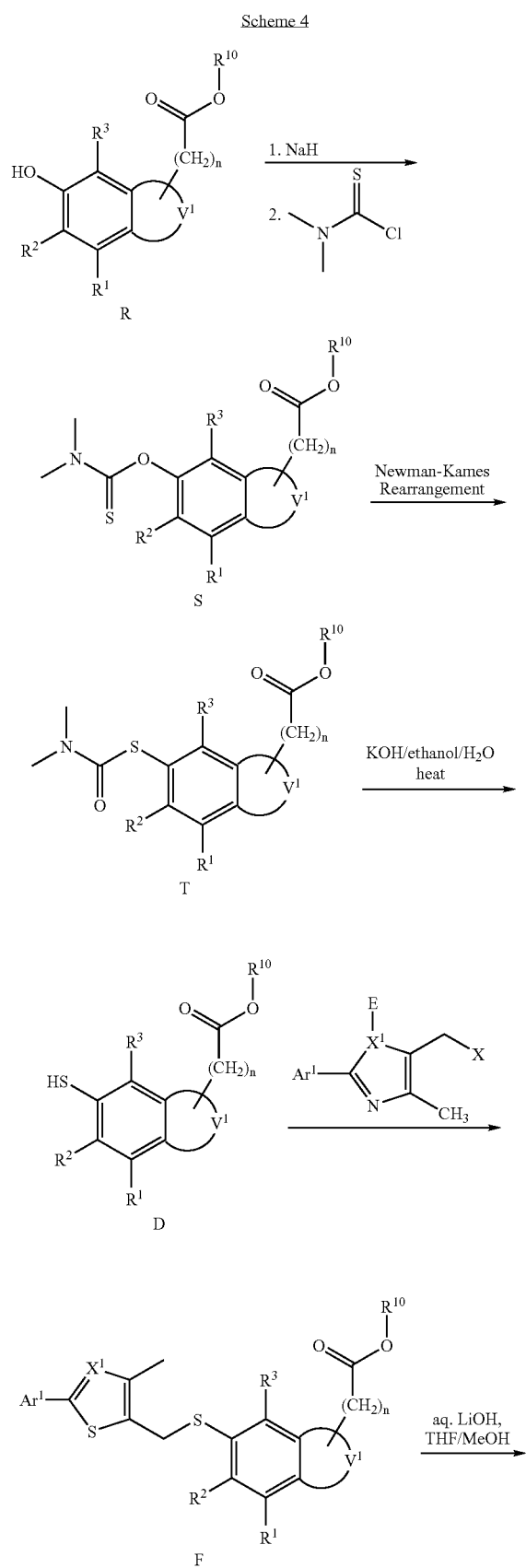

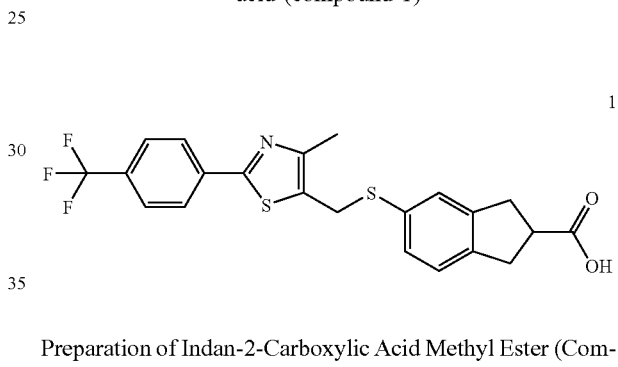

The following non-limiting descriptions also demonstrate methods for the synthesis of compounds of Formula I.

EXAMPLE 1

Synthesis of 5-[4-methyl-2-(4-trifluoromethyl-phenyl)-thiazol-5-ylmethylsulfanyl]-indan-2-carboxylic acid (compound 1)

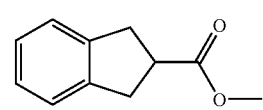

Preparation of Indan-2-Carboxylic Acid Methyl Ester (Compound 1A)

[structure 1A]

Indan-2-carboxylic acid (2.0 g, 12.34 mmol) was dissolved in MeOH (50 mL) and was then treated with $H_2SO_4$ (1 mL). The reaction mixture was refluxed overnight. MeOH was evaporated and the residue was diluted with water and ether. Layers were separated and the aqueous layer was extracted with ether (2×30 mL). The combined organics were dried with $MgSO_4$ and condensed to afford the product (2.01 g, 95%) as white crystals.

MS: 177 $(M+1)^+$

Preparation of 5-Methyl-indan-2-carboxylic acid methyl ester (compound 1B)

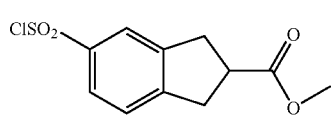

Chlorosulfonic acid (5 mL) was cooled to 0° C. Then compound 1A (1.0 g, 5.68 mmol) was added over 30 min. The mixture was stirred at RT for 3 h and was poured into ice (100 g). The cloudy solution was extracted with ether (2×50 mL). The extracts were dried with magnesium sulfate and concentrated to give a brown oil which was passed through a short pad of silica gel to afford the desired product (1.17 g, 75%) as white plates.

MS: 259 (M−Me)$^+$

Preparation of 5-Mercapto-indan-2-carboxylic acid methyl ester (compound 1C)

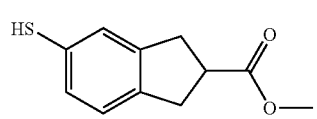

The above product (1.0 g, 3.64 mmol) was refluxed with tin powder (2.2 g, 18.5 mmol) in MeOH (10 mL) and 4M HCl/dioxane (10 mL). After 3 h, the reaction mixture was poured into ice with CH$_2$Cl$_2$ (50 mL). The phases were separated and the aqueous layer was extracted with CH$_2$Cl$_2$ (2×50 mL). The combined organic layers were dried with magnesium sulfate, filtered and evaporated to give the crude thiol compound as a yellow oil (total mass: 830 mg). It was used for the next step without further purification.

MS: 207 (M−1)$^+$

Preparation of 5-[4-Methyl-2-(4-trifluoromethyl-phenyl)-thiazol-5-lmethylsulfanyl]-indan-2-carboxyl acid methyl ester (compound 1D)

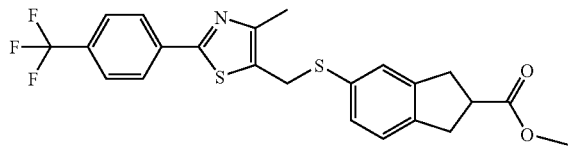

Compound 1C (crude mixture from above, 830 mg) was dissolved in acetonitrile (80 mL) with the chloride 5-chloromethyl-4-methyl-2-(4-trifluoromethyl-phenyl)-thiazole (0.50 g, 1.71 mmol) and Cs$_2$CO$_3$ (2.37 g, 7.27 mmol) The reaction mixture was stirred at RT overnight. Ether (50 mL) and H$_2$O were added and stirring was continued for another 5 min. The layers were separated and the aqueous layer was extracted with ether (2×100 mL). The combined organics was dried over MgSO$_4$ and concentrated to an oil. The crude product was purified by column chromatography eluted with EtOAc and hexanes to give the desired product as a thick yellow oil (0.48 g, 28% for 2 steps).

MS: 464 (M+1)$^+$

Preparation of 5-[4-Methyl-2-(4-trifluoromethyl-phenyl)-thiazol-5-ylmethylsulfanyl]-indan-2-carboxylic acid (compound 1)

To the solution of the above methyl ester (0.46 g, 0.99 mmol) in MeOH (7 mL) and THF (7 mL) was added LiOH.H$_2$O (83 mg, 1.98 mmol). After refluxing overnight, the solution was cooled to RT and solvents were removed by rotavap. The residue was dissolved in water and neutralized with 1N HCl. The cloudy solution was extracted with EtOAc (3×50 mL) and the extracts were dried with MgSO$_4$ and concentrated. The crude product was purified by chromatography to afford a yellow solid, which was further washed with ether to yield the desired product as yellowish crystals (213 mg, 48%).

MS: 450 (M+1)$^+$ CHN: Calc'd: C, 58.78; H, 4.04; N, 3.12. Found: C, 58.45; H, 3.96; N, 2.96.

EXAMPLE 2

Synthesis of {5-[4-methyl-2-(4-trifluoromethyl-phenyl)-thiazol-5-ylmethylsulfanyl]-indan-2-yl}-acetic acid (compound 2)

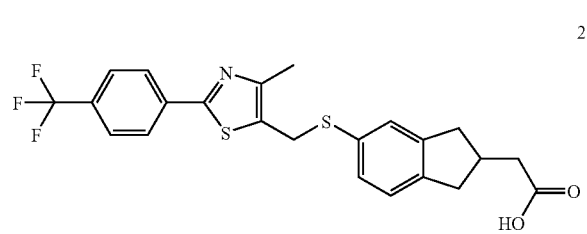

Preparation of indan-2-yl-acetic acid methyl ester (compound 2A)

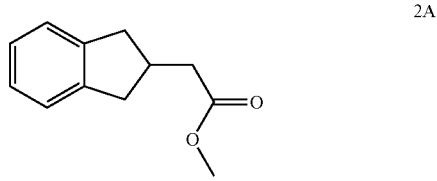

Compound 2A was made following the procedure in Example 1, by replacing Indan-2-carboxylic acid with indan-2-yl-acetic acid. Compound 2A was prepared in 94% yield. NMR ($^1$H, CDCl$_3$): δ 7.15 (5H, m), 3.69 (3H, s), 3.13 (2H, m), 2.88 (1H, m), 2.64 (2H, m), 2.49 (2H, d, j=1.97 hz):

Preparation of (5-chlorosulfonyl-indan-2-yl)-acetic acid methyl ester (compound 2B)

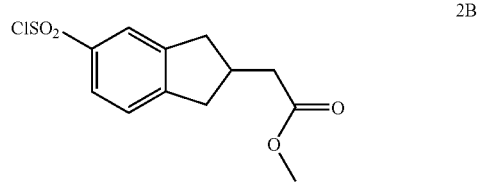

Compound 2B was prepared according to the method of Example 1 utilizing compound 2A. Compound 2B was prepared in 63% yield. MS: 253 (M−Cl)$^+$.

Preparation of (5-Mercapto-indan-2-yl)-acetic acid methyl ester (compound 2C)

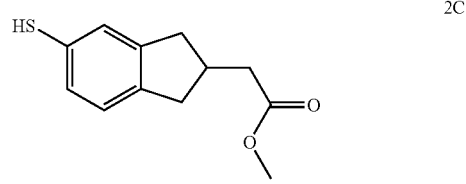

Compound 2C was prepared according to the method of Example 1 utilizing compound 2B. The crude product was used immediately.

Preparation of {5-[4-Methyl-2-(4-trifluoromethyl-phenyl)-thiazol-5-ylmethylsulfanyl]-indan-2-yl}-acetic acid methyl ester (compound 2D)

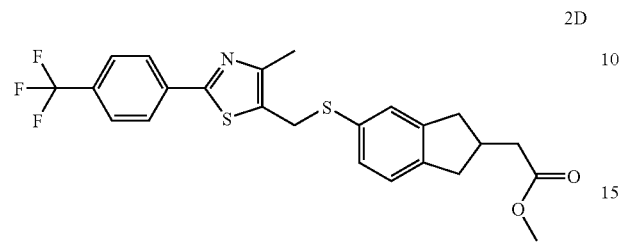

2D

Compound 2D was prepared according to the method of Example 1 utilizing compound 2C. Compound 2D was prepared in 27% yield. MS: 478 (M+1)$^+$.

Preparation of {5-[4-Methyl-2-(4-trifluoromethyl-phenyl)-thiazol-5-ylmethylsulfanyl]-indan-2-yl}-acetic acid (compound 2)

Compound 2 was prepared according to the method of example 1 utilizing compound 2D.

Compound 2 was prepared in 48% yield. MS: 462 (M−1)$^+$

EXAMPLE 3

Synthesis of 6-[4-Methyl-2-(4-trifluoromethyl-phenyl)-thiazol-5-ylmethylsulfanyl]-1-benzopyran-2-carboxylic acid (compound 3)

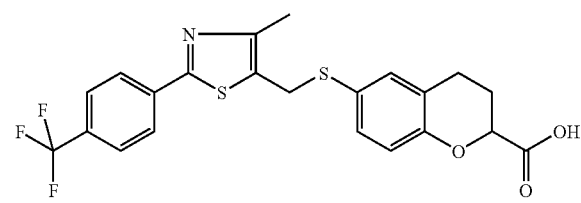

3

Preparation of Chroman-2-carboxylic acid methyl ester (compound 3A)

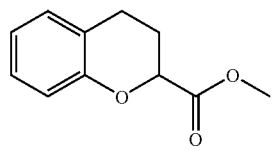

3A

Compound 3A was prepared by hydrogenation of the methyl 4-oxo-4H-chromene-2-carboxylate catalyzed by 10% Pd/C in 93% yield. MS: MS: 193 (M+1)$^+$.

Preparation of 6-Chlorosulfonyl-chroman-2-carboxylic acid methyl ester (compound 3B)

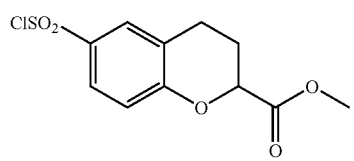

3B

Compound 3B was prepared according to the method of Example 1 utilizing compound 3A. The crude product was used immediately.

Preparation of 6-Mercapto-chroman-2-carboxylic acid methyl ester (compound 3C)

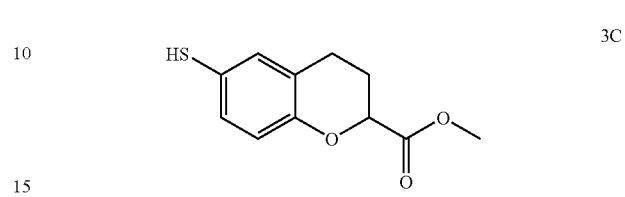

3C

Compound 3C was prepared according to the method of Example 1 utilizing compound 3B. Compound 3C was prepared in 67% yield. MS: 223 (M−1)$^+$.

Preparation of 6-[4-Methyl-2-(4-trifluoromethyl-phenyl)-thiazol-5-ylmethylsulfanyl]-1-benzopyran-2-carboxylic acid methyl ester (compound 3D)

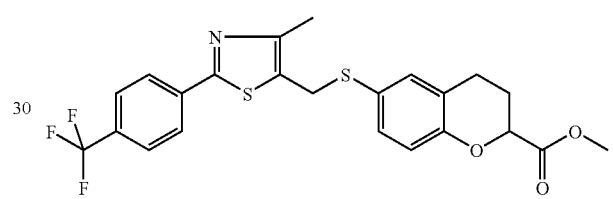

Compound 3D was prepared according to the method of Example 1 utilizing compound 3C. Compound 3D was prepared in 49% yield. MS: 480 (M+1)$^+$.

Preparation of 6-[4-Methyl-2-(4-trifluoromethyl-phenyl)-thiazol-5-ylmethylsulfanyl]-1-benzopyran-2-carboxylic acid (compound 3)

Compound 3 was prepared according to the method of Example 1 utilizing compound 3D. Compound 3 was prepared in 58% yield. MS: 466 (M+1)$^+$

EXAMPLE 4

Synthesis of {5-[4-Methyl-2-(4-trifluoromethyl-phenyl)-thiazol-5-ylmethylsulfanyl]-2,3-dihydro-benzofuran-2-yl}-acetic acid (compound 4)

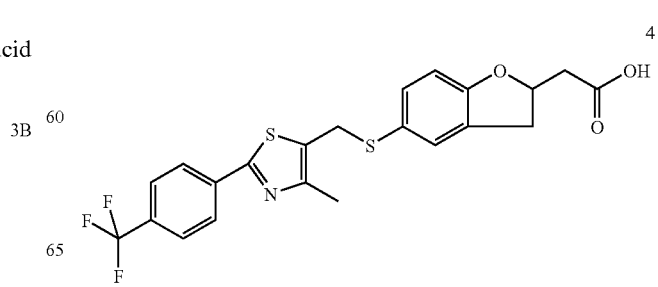

4

Preparation of (2,3-Dihydro-benzofuran-2-yl)-acetic acid methyl ester (compound 4B)

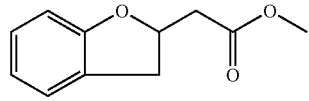

Compound 4B was prepared by hydrogenation of the corresponding tetrahydrofuran derivative catalyzed by 10% Pd/C in 99% yield. MS: MS: 193 (M+1)$^+$.

Preparation of (5-Chlorosulfonyl-2,3-dihydro-benzofuran-2-yl)-acetic acid methyl ester (compound 4C)

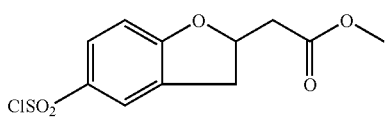

Compound 4C was prepared according to the method of Example 1 utilizing compound 4B. The crude product was used immediately.

Preparation of (5-Mercapto-2,3-dihydro-benzofuran-2-yl)-acetic acid methyl ester (compound 4D)

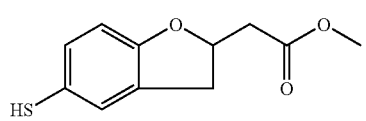

Compound 4D was prepared according to the method of Example 1 utilizing compound 4C. Compound 4D was prepared in 44% yield for 2 steps. MS: 223 (M–1)$^+$.

Preparation of {5-[4-Methyl-2-(4-trifluoromethyl-phenyl)-thiazol-5-ylmethylsulfanyl]-2,3-dihydro-benzofuran-2-yl}-acetic acid methyl ester (compound 4E)

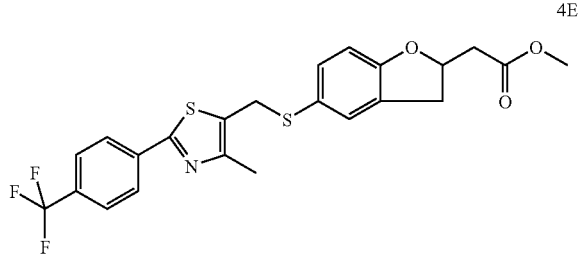

Compound 4E was prepared according to the method of Example 1 utilizing compound 4D in 10% yield. MS: 480 (M+1)$^+$.

Preparation of {5-[4-Methyl-2-(4-trifluoromethyl-phenyl)-thiazol-5-ylmethylsulfanyl]-2,3-dihydro-benzofuran-2-yl}-acetic acid methyl ester (compound 4)

Compound 4 was prepared according to the method of Example 1 utilizing compound 4D in 32% yield. MS: 466 (M+1)$^+$

EXAMPLE 5

Synthesis of {6-[4-methyl-2-(4-trifluoromethyl-phenyl)-thiazol-5-ylmethylsulfanyl]-1-benzopyran-2-acetic acid (compound 5)

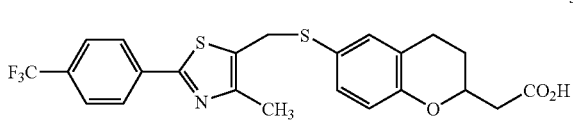

Preparation of Chroman-2-ol (compound 5A)

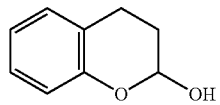

Dihydrocoumarin (5 g, 33.74 mmol) was dissolved in 50 mL of toluene and cooled to –78° C. Dibal (1 M solution in toluene, 38 mL, 38 mmol) was added to the reaction flask over a 45 minutes period. The reaction mixture was stirred at this temperature for 2 h. Water (50 mL) was added slowly along with some toluene to ensure a smooth stirring of the reaction mixture. The slurry was warmed to room temperature and stirring was continued overnight. The organic layer was decanted and dried with magnesium sulfate. Solvent was removed via rotatory evaporator to give compound 5A as a clear oil (4.5 g, 89%). MS: 149 (M–1)$^+$ Preparation of 2-Chroman-2-yl-malonic acid dimethyl ester (compound 5B)

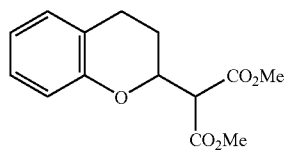

A mixture of 5A (6.77 g, 45 mmol), methyl malonate (16.8 g, 127 mmol), and piperidine (0.8 g, 9.4 mmol) was stirred at 50° C. for 3 h. The reaction was worked up by adding water (150 mL), 1 N HCl (10 mL), and ether (250 mL). Layers were separated and the ether layer was dried with magnesium sulfate. Solvent was concentrated to give compound 5B (5.6 g, 47%) as a clear oil. MS: 265 (M+1)$^+$ Preparation of 2-(6-Mercapto-chroman-2-yl)-malonic acid dimethyl ester (compound 5C)

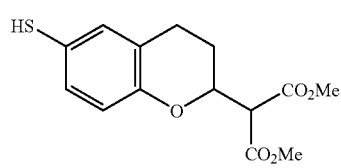

1). Chlorosulfonic acid (15 mL) was cooled to 0° C. Then compound 5B (5.5 g. 20.8 mmol) was added over 30 min.

The mixture was stirred at RT for 3 h and was poured into ice (100 g). The cloudy solution was extracted with ether (2×100 mL). The extracts were dried with magnesium sulfate and concentrated to give the desired product (4.0 g, 53%) as a yellow oil. The crude product was used immediately for the next step without purification.

2). The above product was refluxed with tin powder (10 g, 84 mmol) in MeOH (20 mL) and 4M HCl/dioxane (20 mL). After 3 h, the reaction mixture was poured into ice with $CH_2Cl_2$ (200 mL). The phases were separated and the aqueous layer was extracted with $CH_2Cl_2$ (2×50 mL). The combined organic layers were dried with magnesium sulfate, filtered and evaporated to give the thiol compound 5C as a yellow oil (2.3 g, 37%, 2 steps). MS: 297 $(M+1)^+$ Preparation of {6-[4-Methyl-2-(4-trifluoromethyl-phenyl)-thiazol-5-ylmethylsulfanyl]-1-benzopyran-2-yl}-acetic acid (compound 5)

1). Compound 5C (200 mg, 0.67 mmol) was dissolved in acetonitrile (10 mL) with 5-chloromethyl-4-methyl-2-(4-trifluorometyl-phenyl)-thiazole (200 mg, 0.68 mmol) and $Cs_2CO_3$ (425 mg, 1.3 mmol). The reaction mixture was stirred at RT overnight. Ether (10 mL) was added and stirring was continued for another 5 min. The mixture was filtered and washed with more ether. The filtrate was concentrated and the residue was purified by column chromatography eluted with ether and hexanes to give the desired product as a thick oil (85 mg, 23%). MS: 552 $(M+1)^+$ 2). The above methyl ester was heated to reflux with HBr (48%, 10 mL) for 30 min. The mixture was cooled to RT and HBr was removed by rotatory evaporator. Residue was dissolved in ether (20 mL) and ethyl acetate (5 mL) and treated with 10 drops of saturated $NaHCO_3$. The mixture was stirred at RT overnight and was then filtered through a pad of silica gel. The product, compound 5 crystallized in ether/hexanes (1:1) to give 12 mg white solid. MS: 480 $(M+1)^+$ Alternate Synthesis of {6-[4-Methyl-2-(4-trifluoromethyl-phenyl)-thiazol-5-ylmethylsulfanyl]-1-benzopyran-2-yl}-acetic acid (compound 5)

Preparation of 6-Mercapto-chroman-2-one (compound 5D):

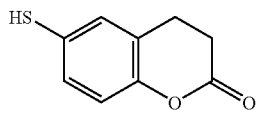

1. To chlorosulfonic acid (15 g, 0.13 mmol) cooled at 0° C. was added dihydrocoumarin (4.5 g, 30 mmol) dropwise. The ice bath was removed and the reaction was continued for another 2 h. The reaction was quenched by pouring the mixture into iced water (150 mL). Layers were separated and the aqueous layer was extract with EtOAc (3×50 mL). Combined organics were dried with $MgSO_4$ and filtered. Solvent was evaporated to afford the sulfonyl cloride derivative as an off-white solid (4.6 g, 61%)

2. Product from above (3.9 g, 15.8 mmol) was refluxed in HCl in dioxane (4 M) with tin powder (12 g, 101 mmol) for 2 h. The reaction mixture was poured into ice-$CH_2Cl_2$ bath. Layers were separated and the aqueous layer was extracted with $CH_2Cl_2$. After drying, solvent was removed to afford the thio product 5D as a white solid (1.56 g, 55%). MS: 179 $(M-1)^+$ Preparation of 6-[4-Methyl-2-(4-trifluoromethyl-phenyl)-thiazol-5-ylmethylsulfanyl]-chroman-2-one (compound 5E):

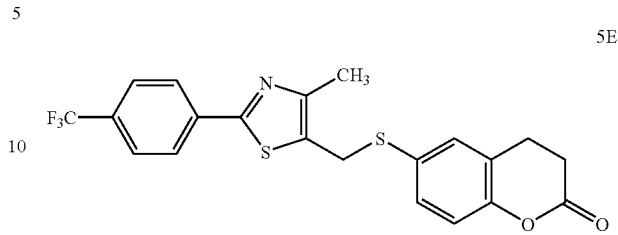

Compound 5D (1.05 g, 5.8 mmol) was dissolved in THF (80 mL) with the 5-chloromethyl-4-methyl-2-(4-trifluoromethyl-phenyl-)-thiazole (1.40 g, 5.0 mmol) and $Cs_2CO_3$ (3.0 g, 9.2 mmol). The reaction mixture was stirred at RT overnight. Ether (50 mL) and $H_2O$ were added and stirring was continued for another 5 min. The layers were separated and the aqueous layer was extracted with ether (2×100 mL). The combined organics was dried over $MgSO_4$ and concentrated to an oil. The crude product was purified by column chromatography eluted with EtOAc and hexanes to give the desired product 5E as an off-white solid (1.1 g, 53%). MS: 436 $(M+1)^+$ Preparation of 6-[4-Methyl-2-(4-trifluoromethyl-phenyl)-thiazol-5-ylmethylsulfanyl]-chroman-2-ol (compound 5F):

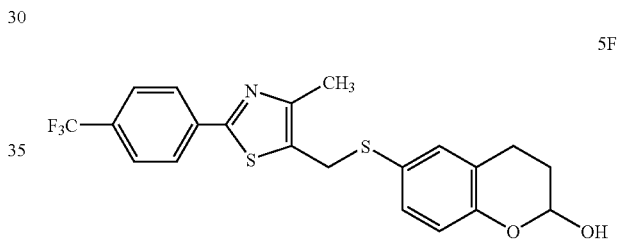

The above compound 5E (200 mg, 0.46 mmol) was dissolved in toluene (25 mL) and was cooled to −78° C. Dibal-H (1 mL, 1 M solution in toluene) was added dropwise and the reaction mixture was stirred at this temperature for 2 h. The reaction was quenched with slow addition of water (0.5 mL) and stirring was continued for another 30 min. After it was warmed to room temperature, the mixture was passed through a short pad of $MgSO_4$. Solvent was removed to afford the product 5F (125 mg, 62%)

MS: 438 $(M+1)^+$

Preparation of {6-[4-Methyl-2-(4-trifluoromethyl-phenyl)-thiazol-5-ylmethylsulfanyl]-1-benzopyran-2-yl}-acetic acid methyl ester (compound 5G):

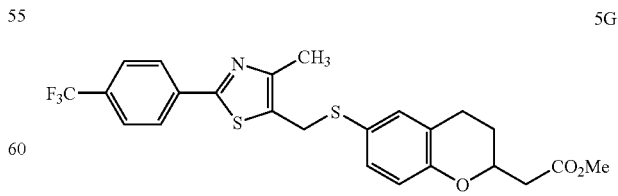

Mixture of compound 5F (130 mg, 0.3 mmol) and methyl (triphenylphosphoranylidene) acetate (110 mg, 0.33 mmol) in CDCl3 (15 mL) was heated to 60° C. for 2 h. After the reaction mixture was cooled to RT, ether (100 mL) was added and the mixture was passed through a short silica gel column eluted with ether. Solvent was removed to afford compound 5G as an off-white solid (95 mg, 65%). MS: 494 (M+1)+

Preparation of {6-[4-Methyl-2-(4-trifluoromethyl-phenyl)-thiazol-5-ylmethylsulfanyl]-1-benzopyran-2-yl}-acetic acid (compound 5)

The above ester 5G (1.6 g, 3.2 mmol) was dissolved in THF (5 mL), MeOH (10 mL), and water (5 mL). It was treated with LiOH.H2O (200 mg, 4.9 mmol) followed by refluxing for 30 min. Solvent was removed and the residue was diluted with EtOAc (75 mL) and ether (15 mL) followed by addition of concentrated HCl. Stirring was continued for 30 min and the solution was passed through a short pad of MgSO4. Solvent was removed and the product was recrystallized with ether to afford the product compound 5 as a white solid (1.2 g, 77%). MS: 494 (M+1)+. CHN: Calc'd: C, 57.6; H, 4.20; N, 2.90. Found: C, 57.6; H, 3.92; N, 2.85.

EXAMPLE 6

Synthesis of 5-[4-methyl-2-(4-trifluoromethyl-phenyl)-thiazol-5-ylmethylsulfanyl]-benzofuran-2-carboxylic acid (compound 6)

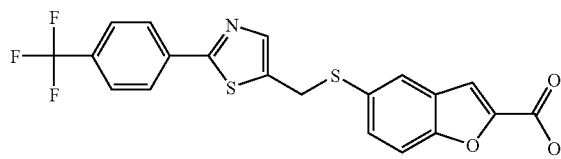

Preparation of 5-Hydroxy-benzofuran-2-carboxylic acid methyl ester (compound 6A)

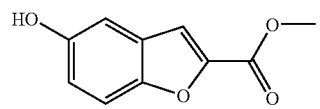

A solution of 5-methoxy-benzofuran-2-carboxylic acid methyl ester (5.0 g, 24 mmol) in 50 mL DCM at 0° C. was treated portionwise with boron tribromide (4.4 mL of a 1 M solution in DCM). After 3 hours, the reaction mixture was carefully quenched with 50% NH4OH. The organic layer was separated and washed 1×50 mL brine, dried (Na2SO4), and concentrated in vacuo to give 2 g (43%) of the title compound pure enough for subsequent use. 400 MHz $^1$H NMR (DMSO-d$_6$) δ 9.47 (s, 1H), 7.56 (s, 1H), 7.45 (d, 1H, J=8.8 Hz), 7.00 (s, 1H), 6.91 (d, 1H,J=8.8 Hz), 3.81 (s, 3H).

Preparation of 5-Dimethylthiocarbamoyloxy-benzofuran-2-carboxylic acid methyl ester (compound 6B)

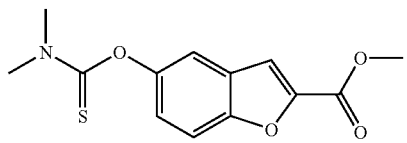

A solution of 5-hydroxy-benzofuran-2-carboxylic acid methyl ester (2 g, 10 mmol) in 50 mL dry DMF was treated portionwise with NaH (252 mg of a 95% dispersion in mineral oil, 10 mmol). After 30 min, dimethylthiocarbamoyl chloride (1.9 g, 15 mmol) was added and the reaction stirred at 40° C. for 1.5 hours. The reaction mixture was then concentrated in vacuo, and the residue taken up in EtOAc. The organic layer was then washed 1×water, 1×brine, dried (Na2SO4) and the solvent removed in vacuo to give 3.5 g of the crude title compound. Recrystallization from CHCl3/hexanes, gave 1.3 g (45%) of the title compound. 400 MHz $^1$H NMR (DMSO-d$_6$) δ 7.72 (s, 1H), 7.68 (d, 1H, J=9.8 Hz), 7.43 (s, 1H), 7.17 (d, 1H,J=9.8 Hz), 3.85 (s, 3H), 3.32 (s, 3H), 3.29 (s, 3H).

Preparation of 5-Dimethylcarbamoylsulfanyl-benzofuran-2-carboxylic acid methyl ester (compound 6C)

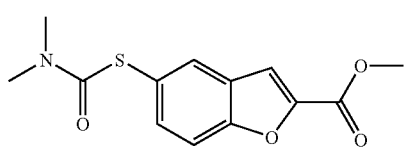

A solution of 5-dimethylthiocarbamoyloxy-benzofuran-2-carboxylic acid methyl ester (1.3 g, 4.7 mmol) in 25 mL diphenyl ether was heated at reflux for 2.5 hours. The reaction mixture was then cooled and the resulting precipitate collected. Purification by flash column chromatography (gradient elution: 100% hexanes to 45% EtOAc/hexanes), gave the title compound (0.58 g, 45%) as a brown solid. 400 MHz $^1$H NMR (DMSO-d$_6$) δ 7.86 (s, 1H), 7.74 (s, 1H), 7.72 (d, 1H, J=9.0 Hz, 7.48 (d, 1H, J=9.0 Hz), 3.85 (s, 3H), 3.36 (s(br), 6H); MS m/z 280 (M+1).

Preparation of 5-Mercapto-benzofuran-2-carboxylic acid methyl ester (compound 6D)

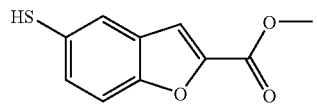

A solution of 5-dimethylcarbamoylsulfanyl-benzofuran-2-carboxylic acid methyl ester (0.5 g, 1.8 mmol) and potassium hydroxide (0.5 g, 12.5 mmol) in 25 ml 2:1 ethanol/water was heated at reflux for 18 hours. The reaction was then cooled, acidified with 2 M HCl, extracted 2×25 mL EtOAc, dried (Na2SO4) and the solvent removed in vacuo to give 350 mg of the crude product. The crude mixture was then refluxed overnight in 25 mL MeOH and catalytic H2SO4. The reaction was then cooled, concentrated in vacuo, taken up in EtOAc and washed with brine. The organic layer was then dried (Na2SO4) and concentrated in vacuo to give 330 mg (95%) of the title compound pure enough for subsequent use. 400 MHz $^1$H NMR (DMSO-d$_6$) δ 7.66 (s, 1H), 7.62 (s, 1H), 7.57(d, 1H, J=9.0 Hz), 7.37 (d, 1H, J=9.0 Hz), 5.49 (s(br), 1H), 3.85 (s, 3H).

Preparation of 5-[4-Methyl-2-(4-trifluoromethyl-phenyl)-thiazol-5-ylmethylsulfanyl]-benzofuran-2-carboxylic acid methyl ester (compound 6E)

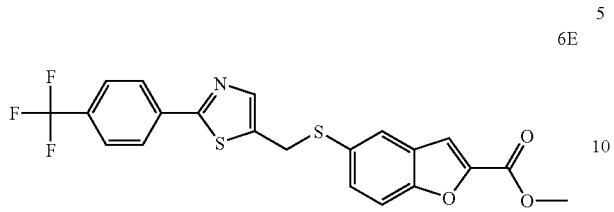

A mixture of 5-mercapto-benzofuran-2-carboxylic acid methyl ester (300 mg, 1.4 mmol) and 5-chloromethyl-4-methyl-2-(4-trifluoromethyl-phenyl)-thiazole (550 mg, 1.9 mmol) was dissolved in 5 ml anhydrous acetonitrile followed by addition of cesium carbonate (700 mg, 2.1 mmol). The reaction was then stirred at 60° C. for 2 hours, filtered and concentrated in vacuo. Purification by flash column chromatography (gradient elution: 5% EtOAc/hexanes to 45% EtOAc/hexanes), gave the title compound (410 mg, 61%) as a pale yellow solid. M.p. 132–133° C.; IR (thin film) cm$^{-1}$: 1173; 400 MHz $^1$H NMR (DMSO-d$_6$) δ 7.95 (d, 2H, J=8.1 Hz), 7.79 (s, 1H), 7.74 (d, 2H, J=8.1 Hz), 7.65 (m, 2H), 7.51 (d, 1H, J=9.0 Hz), 4.44 (s, 2H), 3.82 (s, 3H); MS m/z 464 (M+1); Annl. Calc'd for $C_{22}H_{16}F_3N_1O_3S_2$ C, 57.01; H, 3.48; N, 3.02; found: C, 56.94; H, 3.44; N, 2.84.

Preparation of 5-[4-Methyl-2-(4-trifluoromethyl-phenyl)-thiazol-5-ylmethylsulfanyl]-benzofuran-2-carboxylic acid (compound 6)

The product from example 6E (350 mg, 0.75 mmol), dissolved in 5 ml THF and 1 ml water, was treated with lithium hydroxide monohydrate (159 mg, 3.75 mmol); stirring at room temperature for 1 hour. The reaction mixture was then acidified to about pH 3 with 2 N HCl. The reaction was then extracted into ethyl acetate (2×20 ml). The organic extracts were washed with brine, dried over anhydrous sodium sulfate, decanted, and concentrated. Recrystallization from CHCl$_3$/hexanes, gave 232 mg (68%) of the title compound. M.p. 207–209° C.; IR (thin film) cm$^{-1}$: 1684; 400 MHz $^1$H NMR (DMSO-d$_6$) δ 7.95 (d, 2H, J=8.1 Hz), 7.77 (s, 1H), 7.74 (d, 2H, J=8.1 Hz), 7.62 (d, 1H, J=8.8 Hz), 7.55 (s, H), 7.48 (d, 1H, J=8.8 Hz), 4.43 (s, 2H); MS m/z 448 (M−1); Anal. Calc'd for $C_{21}H_{14}F_3N_1O_3S_2$ C, 56.12; H, 3.14; N, 3.12; found: C, 55.68; H, 3.16; N, 2.98.

EXAMPLE 7

Synthesis of {6-[4-methyl-2-(4-trifluoromethylphenyl)thiazol-5-ylmethylsulfanyl]-1-oxo-3,4-dihydro-1H-naphthlen-2-yl}-acetic acid (Compound 7)

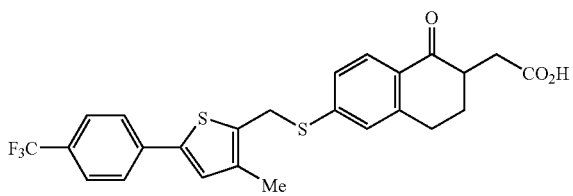

Preparation of Dimethylthiocarbamic acid O-(5-Oxo-5,6,7,8,-tetrahydronaphthalen-2-yl) ester (compound 7A)

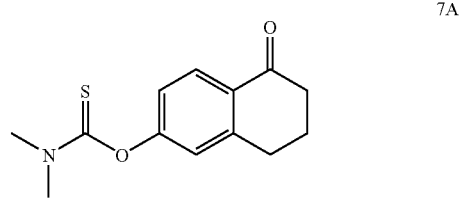

To a solution of 4-hydroxy-1-tetralone (6.5 g, 40 mmol) in Dioxane (75 mL), under nitrogen atmosphere, was added dimethylthiocarbonyl chloride (4.9 g, 40 mmol), triethylamine (5.6 mL, 40 mmol), and DMAP (0.48 g, 3.9 mmol) successively. The resulting mixture was warmed to reflux and refluxed 16 h, then diluted with water (150 mL) and extracted with EtOAc. The combined extracts were washed with water and brine, and the organic phase dried over sodium sulfate then concentrated by roto-vap. The residue was purified by recrystallization in EtOAc/Hexane to give 5.08 g (51%) of brown solid. (mp 126–127° C.) Analyzed for $C_{13}H_{15}NO_2$: Calcd: C, 62.62%; H, 6.06%; N, 5.62%; Found: C, 62.38%; H, 6.02%; N, 5.65%.

To solution of {6-[4-methyl-2-(4-trifluoromethylphenyl)thiazol-5-ylmethylsufanyl]-1-oxo-3,4-dihydro-1H-naphthalen-2-yldene}acetic acid (0.50 g, 1.0 mmol) in chilled glacial acetic acid (3 mL) was added zinc powder (0.30 g, 4.5 mmol). The resulting mixture was stirred 1 h, diluted with water, and extracted with EtOAc. The combined extracts were washed with water and brine, and the organic phase dried over magnesium sulfate and concentrated under vacuum. The residue was purified by recrystallization in methanol to give 0.273 g (54%) of white crystals. (158–159° C.) Analyzed for $C_{24}H_{22}NO_3S_2$: Calcd: 58.64%; H, 4.10%; N, 2.85%; Found: C, 58.94%; H, 3.97%; N, 2.69%.

Preparation of 6-Mecapto-3,4-dihydro-2H-naphthalen-1-one (compound 7B)

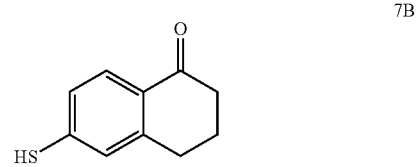

Neat dimethylthiocarbamic acid 0-(5-oxo-5,6,7,8,-tetrahydronaphthalen-2-yl) ester (5.7 g, 23 mmol) was heated to 230–240° C. under nitrogen atmosphere for 1 h, then cooled to room temperature. The residue was dissolved in methanol (100 mL), placed under nitrogen atmosphere, and solution of 50% aqueous sodium hydroxide in water (20 mL) added. The resulting mixture was refluxed for 16 h, cooled to room temperature, acidified with 2N HCL and extracted with EtOAc. The combined extracts were washed with saturated aqueous sodium bicarbonate and brine. The organic phase was dried over sodium sulfate and concentrated under vacuum. The residue was purified by flash chromatography (silica gel, 10% EtOAc/Hexane) to give 3.59 g (89%) of a yellow oil. NMR (400 Mhz, CDCl$_3$) δ

2.08–2.12 (m, 2H), 2.58–2.62 (m, 2H), 2.87 (t, J=6 Hz, 2H) 7.10–7.15 (m, 2H), 7.88 (d, J=8 Hz, 1H). MS: (m+1) 179.

Preparation of 6-[4-Methyl-2-(4-trifluoromethylpheyl)thiazol-5-ylmethylsulfanyl]-3,4-dihydro-2H-naphthalen-1-one (compound 7C)

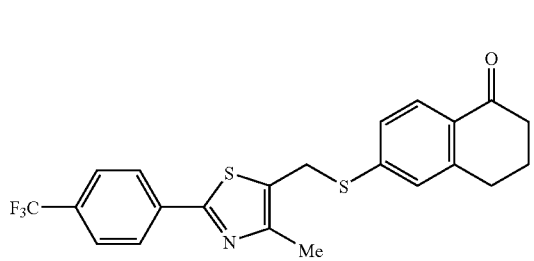

To a solution of 6-mercapto-3,4-dihydro-2H-naphthalen-1-one (3.5 g, 20 mmol) in acetonitrile (100 mL), under nitrogen atmosphere, was added %-chloromethyl-4-methyl-2-(4-trifluoromethylphenyl)thiazole (5.7 g, 20 mmol) followed by cesium carbonate (6.4 g, 20 mmol). The resulting mixture was stirred 16 h, diluted with water (100 mL). The precipitate was collected by filtration, dried, dissolved in EtOAc, and filtered through a plug of silica gel. The filtrate was concentrated under vacuum and the residue purified by recrystallization in iso-propanol to give 5.21 g (61%) of cream colored crystals. (mp 123–124° C.) Analyzed for $C_{22}H_{18}F_3NOS_2$: Calcd: C, 60.95%; H, 4.19%; N, 3.23%; Found: C, 60.79%; H, 4.09%; N, 3.09%.

Preparation of {6-[4-Methyl-2-(4-trifluoromethylphenyl)thiazol-5-ylmethylsulfanyl]-1-oxo-3,4-dihydro-1H-naphthalen-2-ylidene}-acetic acid (compound 7D)

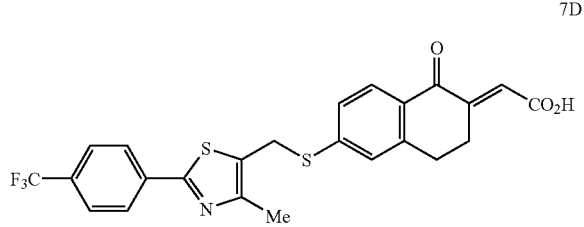

A slurry of 6-[4-methyl-2-(4-trifluoromethylphenyl)thiazol-5-ylmethylsulfanyl]-3,4-dihydro-2H-naphthalen-1-one (2.0 g, 4.6 mmol) in glyoxylic acid monohydrate (2.0 g, 22 mmol), under nitrogen atmosphere, was warmed to 160° C. and stirred for 1 h. The reaction mixture was cooled to room temperature, dissolved in EtOAc (100 mL) and filtered. The filtrate was washed with water (50 mL×3) and brine. The organic phase was dried over magnesium sulfate, concentrated under vacuum, and purified by recrystallization in ethanol to give 1.02 g (45%) of yellow solid. Analyzed for $C_{24}H_{18}NO_3S_2$: Calcd: C, 58.89%; H, 3.71%; N, 2.86%; Found: C, 58.715; H, 3.56%; N, 2.77.

Preparation of {6-[4-Methyl-2-(4-trifluoromethylphenyl)thiazol-5-ylmethylsulfanyl]-1-oxo-3,4-dihydro-1H-naphthalen-2-yl}-acetic acid (Compound 7)

To solution of {6-[4-methyl-2-(4-trifluoromethylphenyl)thiazol-5-ylmethylsufanyl]-1-oxo-3,4-dihydro-1H-naphthalen-2-yldene}acetic acid (0.50 g, 1.0 mmol) in chilled glacial acetic acid (3 mL) was added zinc powder (0.30 g, 4.5 mmol). The resulting mixture was stirred 1 h, diluted with water, and extracted with EtOAc. The combined extracts were washed with water and brine, and the organic phase dried over magnesium sulfate and concentrated under vacuum. The residue was purified by recrystallization in methanol to give 0.273 g (54%) of white crystals. (158–159° C.) Analyzed for $C_{24}H_{22}NO_3S_2$: Calcd: 58.64%; H, 4.10%; N, 2.85%; Found: C, 58.94%; H, 3.97%; N, 2.69%.

EXAMPLE 8

Synthesis of {2-methyl-6-[4-methyl-2-(4-trifluoromethyl-phenyl)-thiazol-5-ylmethylsulfanyl]-chroman-2-yl}-acetic acid (Compound 8)

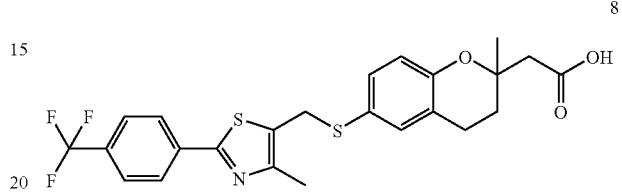

Preparation of (2-Methyl-2H-chromen-2-yl)-acetic acid ethyl ester (compound 8A)

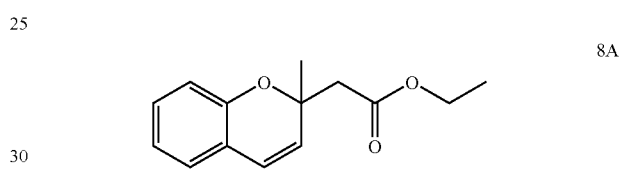

A suspension of 2-hydroxy-3-methylbenzylaldehyde (5.0 g, 40.9 mmol) and diethyl isopropylidenemalonate (8.2 g, 40.9 mmol) in DMF (200 mL) was heated to 135° C. for over night. DMF was removed by rotovap and the residue was treated with water and EtOAc. Layers were separated and the aqueous layer was extracted with EtOAc (100 mL ×3). The combined organics were dried over MgSO4 and filtered. Solvent was removed and the crude product was purified through silica gel column to give the desired product as a white solid (5.98 g, 63%). MS 233 (M+1)$^+$ Preparation of (2-Methyl-chroman-2-yl)-acetic acid ethyl ester (compound 8B)

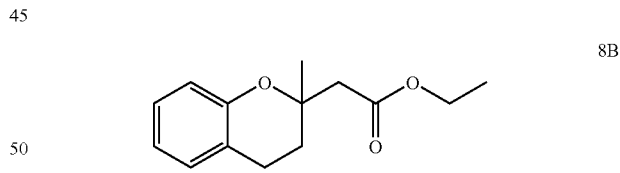

Compound 8A was hydrogenated in MeOH using 10% Pd/C as catalyst. The mixture was then filtered and washed with EtOAc. Solvent was dried to give the product as a thick oil (3.7 g, 100%). MS 235 (M+1)$^+$ Preparation of (6-chlorosulfonyl-2-methyl-chroman-2-yl)-acetic acid ethyl ester (Compound 8C)

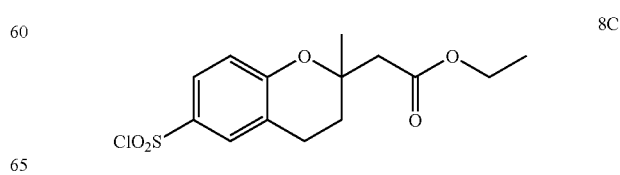

Compound 8B (4.94 g, 21 mmol) was dissolved in CHCl$_3$ (100 mL) and the solution was cooled to 0° C. Chlorosulfonic acid (4.92 g, 42 mmol) was added dropwise. The reaction mixture was stirred at 0° C. for 30 min. followed by RT for 3 h. Quench the reaction with ice. Extractive work up followed by column chromatography gave the product as a yellowish oil (300 mg, 4%). MS 331 (M−1)⁺

Preparation of (6-Mercapto-2-methyl-chroman-2-yl)-acetic acid ethyl ester (Compound 8D)

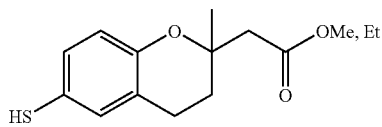

8D

Compound 8D was made the same way as IC 92% yield as a mixture of the methyl (major) and ethyl esters (minor). MS 265 (M+1, Et ester)⁺, MS 251 (M+1, Me ester)⁺

Preparation of {2-Methyl-6-[4-methyl-2-(4-trifluoromethyl-phenyl)-thiazol-5-ylmethylsulfanyl]-chroman-2-yl}-acetic acid methyl/ethyl esters (Compound 8E)

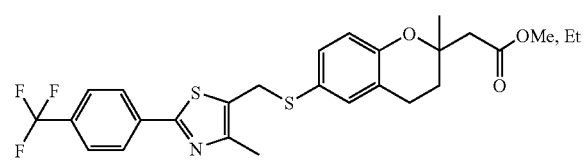

8E

Compound 8E was made the same way as 1D in 41% yield. The mixture was mainly methyl ester with trace of the ethyl ester. MS 508 (M+1, Me ester)⁺, MS 5221 (M+1, Et ester)⁺

Preparation of {2-Methyl-6-[4-methyl-2-(4-trifluoromethyl-phenyl)-thiazol-5-ylmethylsulfanyl]-chroman-2-yl}-acetic acid (Compound 8)

Compound 8 was made from Compound 8E the same way as 1E in 58% yield. MS 494 (M+1)⁺

EXAMPLE 9

Synthesis of {2,8-Dimethyl-6-[4-methyl-2-(4-trifluoromethyl-phenyl)-thiazol-5-ylmethylsulfanyl]-chroman-2-yl}-acetic acid (Compound 9)

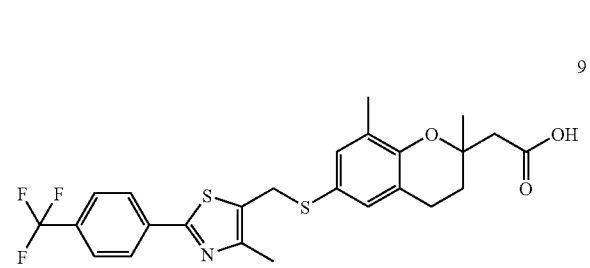

9

Preparation of (2,8-Dimethyl-chromen-2-yl)-acetic acid ethyl ester (compound 9A)

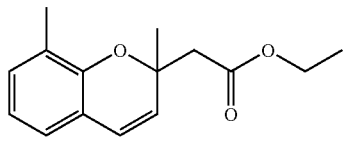

9A

Compound 9A was made similar to 1A in 73% yield. MS 247 (M+1)⁺

Preparation of (2,8-Dimethyl-chroman-2-yl)-acetic acid ethyl ester (compound 9B)

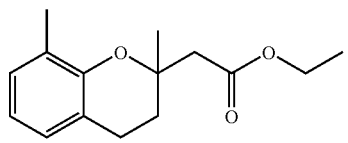

9B

Compound 9B was made similar to 1B in 83% yield. MS 249 (M+1)⁺

Preparation of (6-chlorosulfonyl-2,8-dimethyl-chroman-2-yl)-acetic acid ethyl ester (Compound 9C)

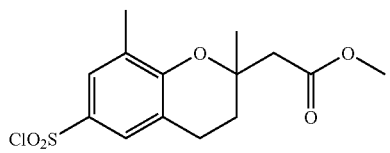

9C

Compound 9C was made similar to 1C in 96% yield. MS 311 (M−Cl)⁺

Preparation of (6-Mercapto-2,8-dimethyl-chroman-2-yl)-acetic acid methyl ester (Compound 9D)

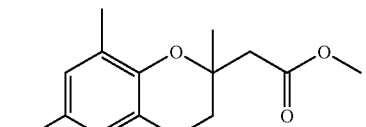

9D

Compound 9D was made the same way as 1C using MeOH as solvent in 90% yield. The ethyl ester was completely transesterified to the methyl ester. MS 266, M+

Preparation of {2,8-Dimethyl-6-[4-methyl-2-(4-trifluoromethyl-phenyl)-thiazol-5-ylmethylsulfanyl]-chroman-2-yl}-acetic acid methyl ester (Compound 9E)

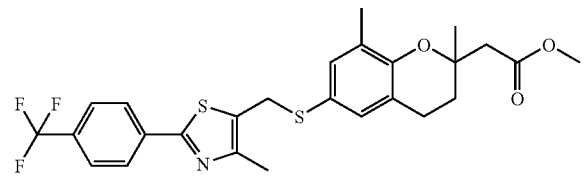

Compound 9E was made the same way as 1D in 75% yield. MS 522 (M+1)+

Preparation of {2,8-Dimethyl-6-[4-methyl-2-(4-trifluoromethyl-phenyl)-thiazol-5-ylmethylsulfanyl]-chroman-2-yl}-acetic acid (Compound 9)

Compound 9 was made the same way as 1E in 50% yield. MS 508 (M+1)+

EXAMPLE 10

Synthesis of {6-[4-Methyl-2-(4-trifluoromethyl-phenyl)-thiazol-5-ylmethylsulfanyl]-3,4-dihydro-1H-isoquinolin-2-yl}-acetic acid (Compound 10)

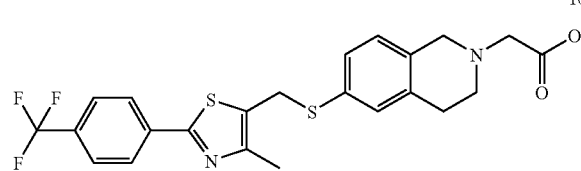

Preparation of (3,4-dihydro-1H-isoquinolin-2-yl)-acetic acid methyl ester (Compound 10A)

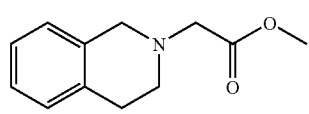

Methyl bromoacetate (6.32 g, 41.3 mmol) was slowly added to a stirred solution of sodium hydride (1.65 g, 41.3 mmol) and 1,2,3,4-tetrahydroisoquinoline (5.0 g, 37.5 mmol). The mixture was stirred at RT for 3 hr. After removing the solvent, the residue was diluted with water and ether. Layers were separated and the aqueous layer was extracted with ether (3×50 ml). The combined organics were dried with MgSO4 and condensed to afford the desired product 10A (5.29 g, 69%) as a yellow oil. MS: 206 (M+1)+.

Preparation of (6-Chlorosulfonyl-3,4-dihydro-1H-isoquinolin-2-yl)-acetic acid methyl ester (Compound 10B)

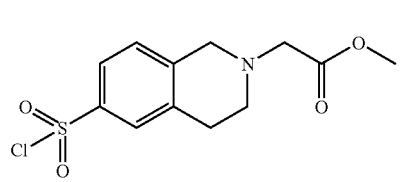

10B was prepared analogously to compound 1B. 24% yield. MS: 304 (M+1)+.

Preparation of (6-Mercapto-3,4-dihydro-1H-isoquinolin-2-yl)-acetic acid methyl ester (Compound 10C)

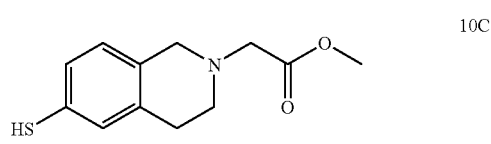

10C was prepared analogously to compound 1C. 74% yield. MS: 238 (M+1)+.

Preparation of {6-[4-Methyl-2-(4-trifluoromethyl-phenyl)-thiazol-5-ylmethylsulfanyl]-3,4-dihydro-1H-isoquinolin-2-yl}-acetic cid methyl ester (Compound 10D)

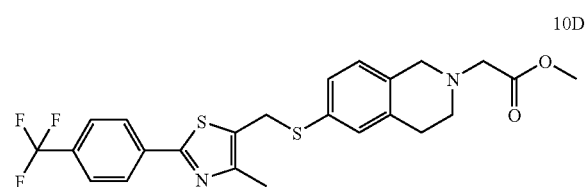

Compound 10D was prepared analogously to compound 1D. Yield was 6% after flash column purification. MS: 493 (M+1)+.

Preparation of {6-[4-Methyl-2-(4-trifluoromethyl-phenyl)-thiazol-5-ylmethylsulfanyl]-3,4-dihydro-1H-isoquinolin-2-yl}-acetic acid (Compound 10)

Compound 10D was prepared analogously to compound 1D. Compound 10 was prepared in 4% yield. MS: 479 (M+1)+.

EXAMPLE 11

Synthesis of {6-[4-methyl-2-(4-trifluoromethyl-phenyl)-thiazol-5-ylmethylsulfanyl]-3,4-dihydro-2H-quinolin-1-yl}-acetic acid (Compound 11)

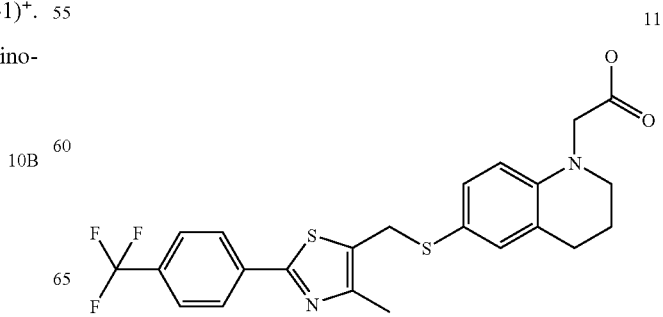

Preparation of (3,4-Dihydro-2H-quinolin-1-yl)-acetic acid methyl ester (compound 11A)

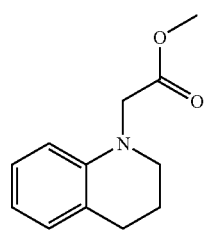

11A was prepared analogously to compound 1A. 99% yield. MS: 206 (M+1)+.

Preparation of (6-chlorosulfonyl-3,4-dihydro-2H-quinolin-1-yl)-acetic acid methyl ester (Compound 11B)

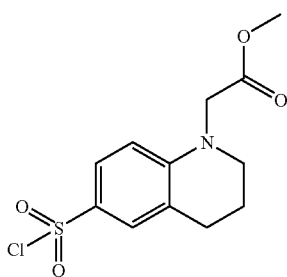

11B was prepared analogously to compound 1B. 12% yield. MS: 304 (M+1)+.

Preparation of (6-Mercapto-3,4-dihydro-2H-quinolin-1-yl)-acetic acid methyl ester (Compound 11C)

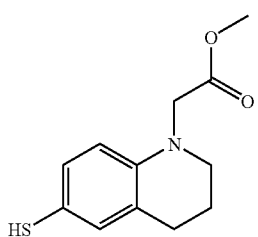

11C was prepared analogously to compound 1C. Used as unpurified oil. MS: 238 (M+1)+.

Preparation of {6-[4-Methyl-2-(4-trifluoromethyl-phenyl)-thiazol-5-ylmethylsulfanyl]-3,4-dihydro-2-quinolin-1-yl}-acetic acid methyl ester (Compound 11D)

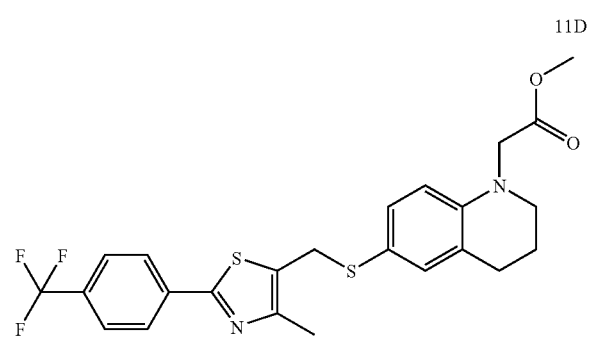

Compound 11D was prepared analogously to compound 1D. Yield was 40% after flash column purification. MS: 493 (M+1)+.

Preparation of {6-[4-Methyl-2-(4-trifluoromethyl-phenyl)-thiazol-5-ylmethylsulfanyl]-3,4-dihydro-2H-isoquinolin-1-yl}-acetic acid (Compound 11)

Compound 11 was prepared analogously to compound 1. Compound 11 was prepared in 4% yield. MS: 479 (M+1)+.

EXAMPLE 12

Synthesis of {6-[4-methyl-2-(4-trifluoromethyl-phenyl)-thiazol-5-ylmethylsulfanyl]-2-oxo-3,4-dihydro-2H-isoquinolin-1-acetic acid (Compound 12)

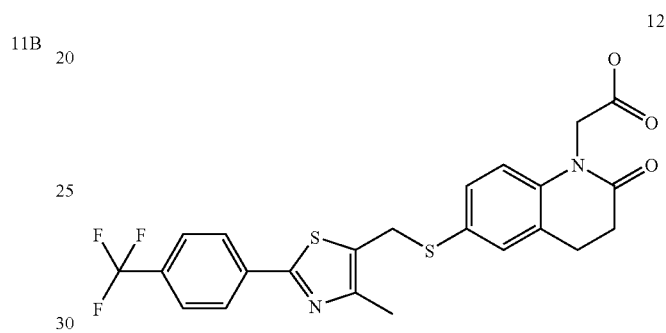

Preparation of (2-Oxo-3,4-dihydro-2H-quinolin-1-yl)-acetic acid methyl ester (Compound 12A)

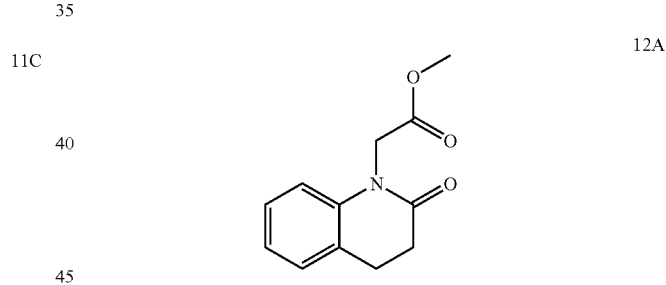

12A was prepared analogously to compound 1A. 95% yield. MS: 220 (M+1)+.

Preparation of (6-chlorosulfonyl-2-oxo-3,4-dihydro-2H-quinolin-1-yl)-acetic acid methyl ester (Compound 12B)

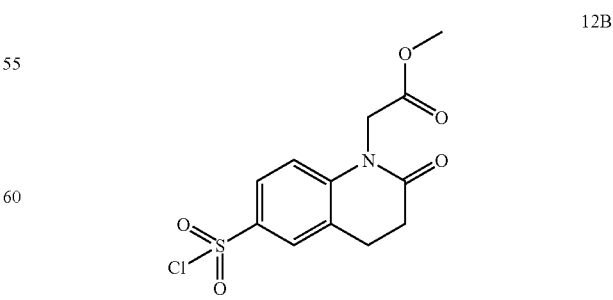

12B was prepared analogously to compound 1B. 11% yield. MS: 318 (M+1)+.

Preparation of (6-Mercapto-2-oxo-3,4-dihydro-2H-Quinolin-1-yl)-acetic acid methyl ester (Compound 12C)

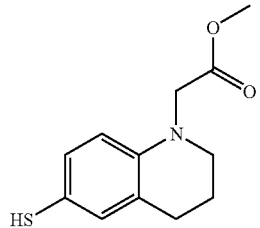

12C was prepared analogously to compound 1C. 92% yield. MS: 252 (M+1)$^+$.

Preparation of {6-[4-Methyl-2-(4-trifluoromethyl-phenyl)-thiazol-5-ylmethylsulfanyl]-2-oxo-3,4-dihydro-2-quinolin-1-yl}-acetic acid methyl ester (Compound 12D)

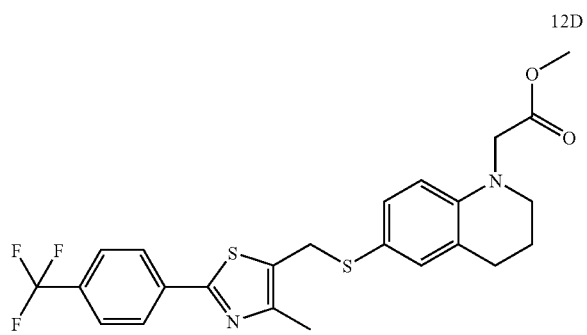

Compound 12D was prepared analogously to compound 1D. Yield was 36%. MS: 507 (M+1)$^+$.

Preparation of {6-[4-Methyl-2-(4-trifluoromethyl-phenyl)-thiazol-5-ylmethylsulfanyl]-2-oxo-3,4-dihydro-2H-isoquinolin-1-yl}-acetic acid (Compound 12)

Compound 12 was prepared analogously to compound 1. Compound 12 was prepared in 70% yield. MS: 493 (M+1)$^+$.

EXAMPLE 13

Synthesis of {7-Methoxy-6-[4-methyl-2-(4-trifluoromethyl-phenyl)-thiazol-5-ylmethylsulfanyl]-1,2,3,4-tetrahydro-naphthalen-2-yl}-acetic acid (Compound 13)

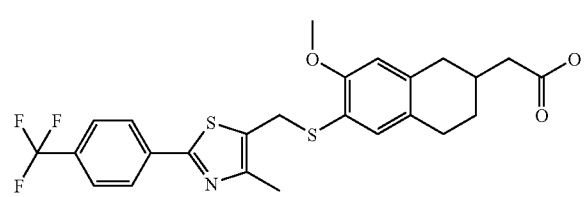

Preparation of (7-Methoxy-1,2,3,4-tetrahydro-naphthalen-2-yl)-acetic acid ethyl ester (Compound 13A)

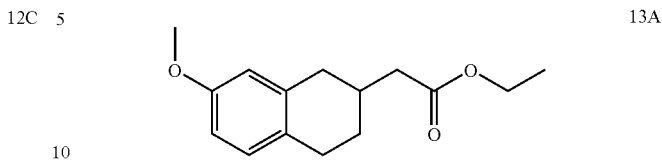

7-Methoxy-2-tetralone (4.5 g, 25.5 mmol) in 25 ml THF was added to a stirred solution of 1.6 M n-butyl lithium (24 ml) and triethyl phosphonoacetate (8.59 g, 38.3 mmol) in 100 ml THF. The mixture was stirred at RT overnight. Water (100 ml) was then added and the layers were separated. The aqueous layer was extracted with ether (2×50 ml). The combined organics was dried with MgSO$_4$ and evaporated to give a dark oil. It was purified by silica gel chromatography eluted with 20% EtOAc/Hexanes to afford the pure product as a yellow oil (5.5 g, 88%).

Compound 13A was then prepared by hydrogenation of the unsaturated oil catalyzed by Pd/C (20%) in 90% yield. MS: 249 (M+1)$^+$.

Preparation of (6-chlorosulfonly-7-methoxy-1,2,3,4-tetrahydro-naphthalen-2-yl) acetic acid ethyl ester (Compound 13B)

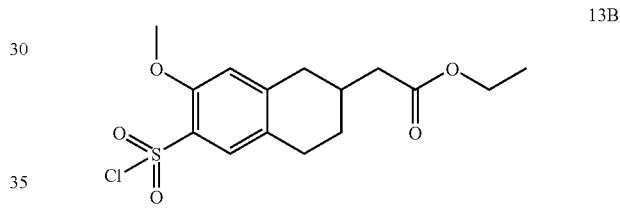

13B was prepared analogously to compound 1B. 59% yield. MS: 311 (M-cl)$^+$.

Preparation of (6-Mercapto-7-methoxy-1,2,3,4-tetrahydro-naphthalen-2-yl)-acetic acid methyl ester (Compound 13C)

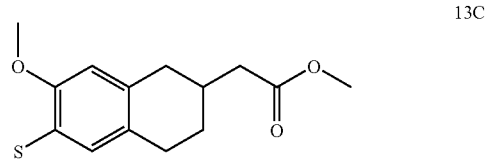

13C was prepared analogously to compound 1C. Yield was 34% after flash column purification. MS: 265 (M-1)$^+$.

Preparation of {7-Methoxy-6-[4-methyl-2-(4-trifluoromethyl-phenyl)-thiazol-5-ylmethylsulfanyl]-1,2,3,4-tetrahydro-naphthalen-2-yl}-acetic acid methyl ester (Compound 13D)

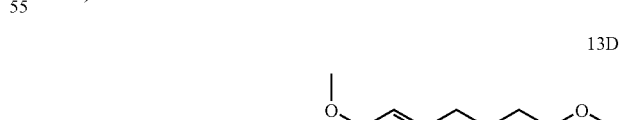

Compound 13D was prepared analogously to compound 1D. Yield was 23% after flash column purification. MS: 522 (M+1)$^+$.

Preparation of {7-Methoxy-6-[4-methyl-2-(4-trifluoromethyl-phenyl)-thiazol-5-ylmethylsulfanyl]-1,2,3,4-tetrahydro-naphthalen-2-yl}-acetic acid (Compound 13)

Compound 13 was prepared analogously to compound 1. Compound 13 was prepared in 81% yield. MS: 508 (M+1)$^+$.

EXAMPLE 14

Synthesis of 7-methoxy-6-[4-methyl-2-(4-trifluoromethyl-pheny)-thiazol-5-ylmethylsulfanyl]-chroman-2-yl-acetic acid (Compound 14)

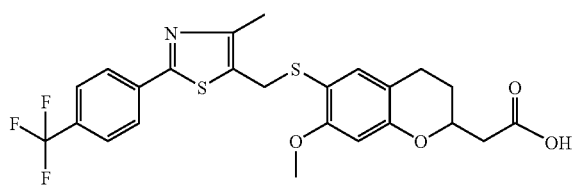

14

Preparation of 7-Methoxy-chroman-2-one (Compound 14A)

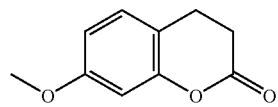

14A

Compound 14A was prepared by hydrogenation of 7-methoxy-chromen-2-one catalyzed by 10% Pd/C in 96% yield. MS: 179 (M+1)$^+$.

Preparation of 3-(2-Hydroxy-4-methoxy-5-thiocyanato-phenyl)-propionic acid methyl ester (Compound 14B)

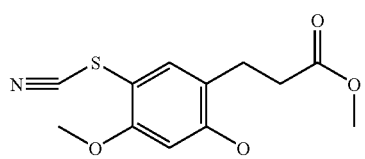

14B

Compound 14A (3 g), KSCN (4.9 g) were dissolved in MeOH (125 mL) at 0° C., Br$_2$ (3 g) was added, then stirred for 2 h. The reaction mixture was quenched with water (200 mL) and ethyl acetate (200 mL). The ethyl acetate was separated and washed with water, brine, dried (MgSO$_4$), concentrated, to afford compound 14B (3.5 g). mp 105–016° C.;

MS: 268 (M+1)$^+$.

Preparation of 6-Mercapto-7-methoxy-chroman-2-ol (Compound 14C)

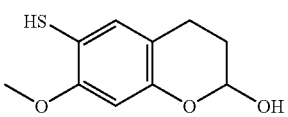

14C

Compound 14B (3.5 g) was dissolved in 500 mL of toluene and cooled to −78° C. Dibal (1M solution in toluene, 40 mL) was added to the reaction over 30 minutes period.

The reaction mixture was stirred at this temperature for 2 h. Water (10 mL) was added slowly, the slurry was warmed to room temperature, and stirring was continued overnight. The organic layer was decanted and dried (MgSO$_4$). Solvent was removed to give compound 14C as a oil (2.2 g). MS: 211(M−1)$^+$.

Preparation of 6-Mercapto-7-methoxy-chroman-2-yl-acetic acid methyl ester (Compound 14D)

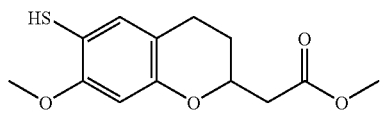

14D

Mixture of compound 14C (2.2 g) and methyl-triphenyl-phosphoranylidene-acetate (2.2 g) in CDCl$_3$ (25 mL) was heated to 60° C. for 3 h. After cooled to RT, ether was added and the mixture was passed through a short silical gel column, eluted with ether. Solvent was removed to afford compound 14D, as a oil (150 mg). MS: 267 (M−1)$^+$.

Preparation of 7-Methoxy-6-[4-Methyl-2-(4-trifluoromethyl-pheny)-thiazol-5-ylmethylsulfanyl]-chroman-2-yl-acetic acid methyl ester (Compound 14E)

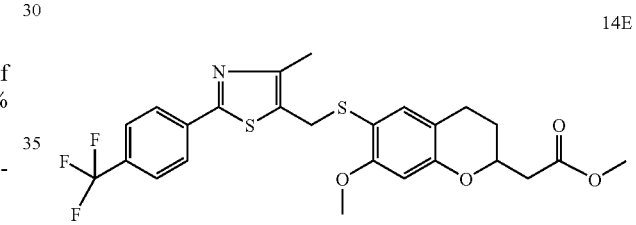

14E

Compound 14E was prepared according to the method of example 1D utilizing compound 14D. Compound 14E was prepared in 20% yield. MS: 524 (M+1)$^+$.

Preparation of 7-Methoxy-6-[4-methyl-2-(4-trifluoromethyl-pheny)-thiazol-5-ylmethylsulfanyl]-chroman-2-yl-acetic acid (Compound 14)

Compound 14 was prepared according to the method of example 1 utilizing compound 14E. MS: 510 (M+1)$^+$.

EXAMPLE 15

Synthesis of 7-Methyl-6-[4-methyl-2-(4-trifluoromethyl-pheny)-thiazol-5-ylmethylsulfanyl]-chroman-2-yl-acetic acid (Compound 15)

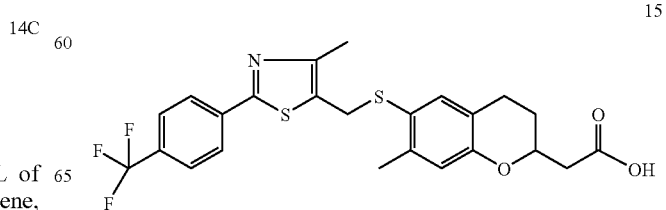

15

Preparation of 7-Methyl-chroman-2-one (Compound 15A)

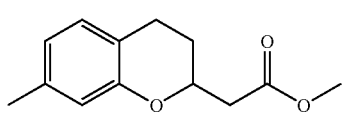

Compound 15A was prepared according to the method of example 1A utilizing compound 7-methyl-chromen-2-one. MS: 163 (M+1)⁺.

Preparation of 3-(2-Hydroxy-4-methyl-5-thiocyanato-phenyl)-propionic acid methyl ester (Compound 15B)

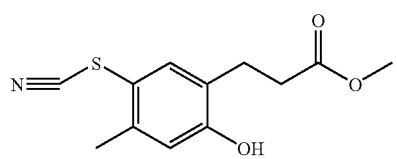

Compound 15B was prepared according to the method of example 1B utilizing compound 15A. MS: 252 (M+1)⁺.

Preparation of 6-Mercapto-7-methyl-chroman-2-ol (Compound 15C)

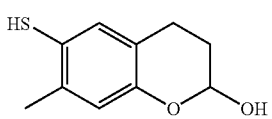

Compound 15C was prepared according to the method of example 1C utilizing compound 15B. MS: 195 (M−1)⁺.

Preparation of 6-Mercapto-7-methyl-chroman-2-yl-acetic acid methyl ester (Compound 15D)

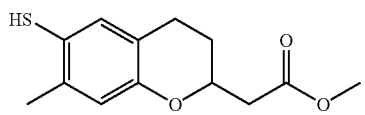

Compound 15D was prepared according to the method of example 1D utilizing compound 15C. MS: 251 (M−1)⁺.

Preparation of 7-Methyl-6-[4-methyl-2-(4-trifluoromethyl-pheny)-thiazol-5-ylmethylsulfanyl]-chroman-2-yl-acetic acid methyl ester (Compound 15E)

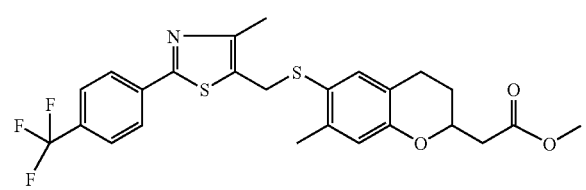

Compound 15E was prepared according to the method of example 1D utilizing compound 15D. Compound 15E was prepared in 45% yield. MS: 508 (M+1)⁺.

Preparation of 7-Methyl-6-[4-methyl-2-(4-trifluoromethyl-pheny)-thiazol-5-ylmethylsulfanyl]-chroman-2-yl-acetic acid (Compound 15A)

Compound 15 was prepared according to the method of example 1 utilizing compound 15E. Compound 15 was prepared in 30% yield. MS: 494 (M+1)⁺.

EXAMPLE 16

Synthesis of 6-[4-methyl-2-(4-trifluoromethyl-pheny)-thiazol-5-ylmethylsulfanyl]-2H-chromene-3-carboxylic acid (Compound 16)

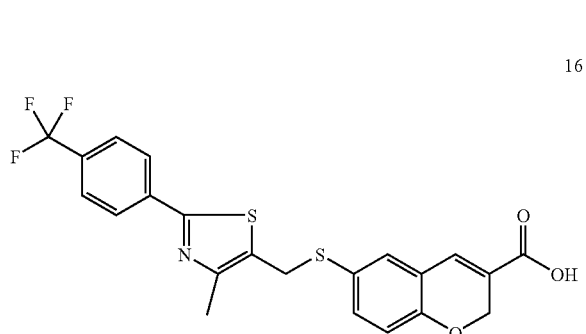

Preparation of 2H-Chromene-3-carbonitrile (Compound 16A)

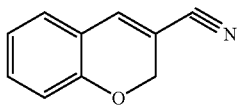

2-Hydroxy-benzaldehyde (14 g), acrylate nitrile (30.5 g) and DABCO (5.1 g) were heated to reflux for 24 h. The reaction mixture was cooled, concentrated. The crude oil was mixed with ether (300 mL) and 2N HCl (200 mL), stirred for 30 minutes. The ether layer was washed with water, brine, dried (MgSO₄), concentrated to afford a oil compound 16A (16.8 g). MS: 158 (M+1)⁺.

Preparation of 2H-chromene-3-carboxylic acid (Compound 16B)

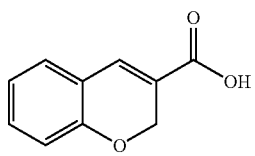

Compound 16A (16.8 g), 10% NaOH (500 mL) were heated to reflux for 12 h. The reaction mixture was cooled to 0° C., acidified with concentrated HCl till pH 2. The product was precipitated, filtered, dried under vacuum, to afford compound 16B, an off-white solid (13.3 g). MS: 177 (M+1)⁺.

Preparation of 2H-Chromene-3-carboxylic acid methyl ester (Compound 16C)

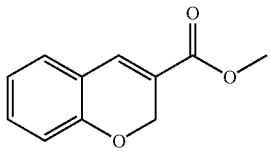

Compound 16B (5 g) and concentrated HCl (2 mL) in MeOH (200 mL) were heated to reflux for 30 h. The reaction mixture was quenched with water (200 mL) and ether (200 mL). Separated the organic layer, washed with water, brine, dried (MgSO$_4$), concentrated to give an off-white solid, compound 16C (4.2 g). mp 56–57° C.; MS: 191 (M+1)$^+$.

Preparation of 6-Chlorosulfonyl-2H-chromene-3-carboxylic acid methyl ester (Compound 16D)

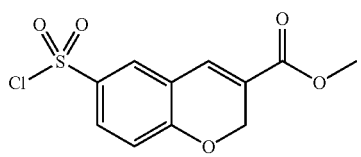

Compound 16D was prepared according to the method of example 1B utilizing compound 16C. The crude product was used immediately.

Preparation of 6-Mercapto-2H-chromene-3-carboxylic acid methyl ester (Compound 16E)

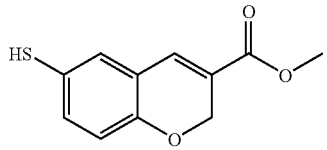

Compound 16E was prepared according to the method of example 1C utilizing compound 16D. Compound 16E was prepared in 20% yield. MS: 221 (M–1)$^+$.

Preparation of 6-[4-Methyl-2-(4-trifluoromethyl-pheny)-thiazol-5-ylmethylsulfanyl]-2H-chromene-3-carboxylic acid methyl ester (Compound 16F)

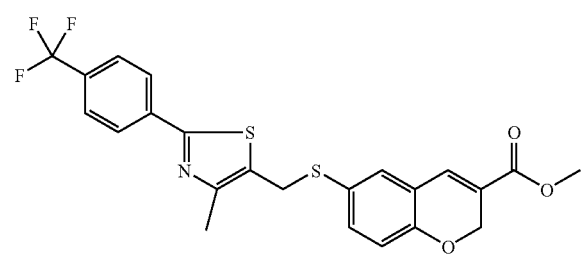

Compound 16F was prepared according to the method of example 1D utilizing compound 16E. Compound 16F was prepared in 45% yield. MS: 478 (M+1)$^+$.

Preparation of 6-[4-Methyl-2-(4-trifluoromethyl-pheny)-thiazol-5-ylmethylsulfanyl]-2H-chromene-3-carboxylic acid (Compound 16)

Compound 16 was prepared according to the method of example 1 utilizing compound 16F. Compound 16 was prepared in 30% yield. MS: 464 (M+1)$^+$.

EXAMPLE 17

Synthesis of 6-[4-methyl-2-(4-trifluoromethyl-pheny)-thiazol-5-ylmethylsulfanyl]-chroman-3-carboxylic acid (Compound 17)

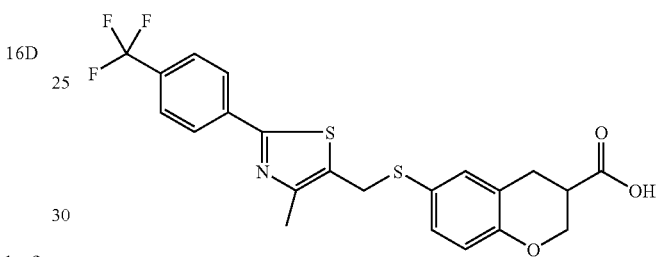

Preparation of Chroman-3-carboxylic acid methyl ester (Compound 17A)

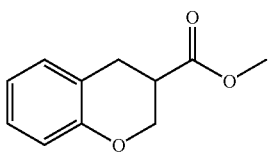

Compound 17A was prepared according to the method of example 3A utilizing compound 16C. Compound 17A was prepared in 95% yield. MS: 193 (M–1)$^+$.

Preparation of 6-chlorosulfonyl-chroman-3-carboxylic acid methyl ester (Compound 17B)

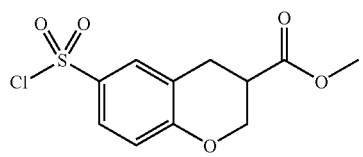

Compound 17B was prepared according to the method of example 1B utilizing compound 17A. The crude product was used immediately.

Preparation of 6-Mercapto-chroman-3-carboxylic acid methyl ester (Compound 17C)

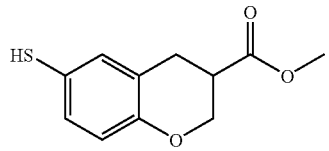

Compound 17C was prepared according to the method of example 1C utilizing compound 17B. Compound PPC was prepared in 85% yield. mp 83–84° C.; MS: 223 (M–1)⁺.

Preparation of 6-[4-Methyl-2-(4-trifluoromethyl-pheny)-thiazol-5-ylmethylsulfanyl]-chroman-3-carboxylic acid methyl ester (Compound 17D)

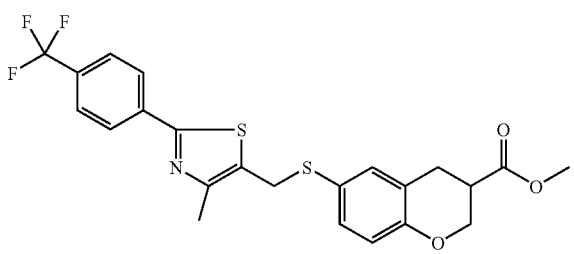

Compound 17D was prepared according to the method of example 1D utilizing compound 17C. Compound 17D was prepared in 45% yield. MS: 480 (M+1)⁺.

Preparation of 6-[4-Methyl-2-(4-trifluoromethyl-pheny)-thiazol-5-ylmethylsulfanyl]-chroman-3-carboxylic acid (Compound 17)

Compound 17 was prepared according to the method of example 1 utilizing compound 17D. Compound 17 was prepared in 65% yield. mp 139–140° C.; MS: 466 (M+1)⁺.

EXAMPLE 18

Synthesis of 6-[4-methyl-2-(4-trifluoromethyl-pheny)-thiazol-5-ylmethylsulfanyl]-chroman-3-yl-acetic acid (Compound 18)

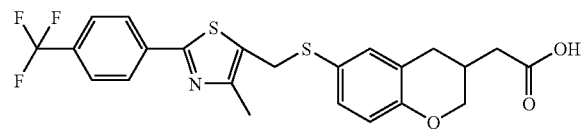

Preparation of Chroman-3-yl-methanol (Compound 18A)

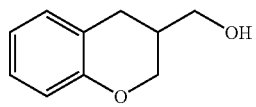

Compound 17A (3 g) was dissolved in 300 mL of toluene at –78° C. DibalH (1M solution in toluene, 32 mL) was added to the reaction over 30 minutes period. The reaction mixture was stirred at this temperature for 2 h. 2N NaOH (5 mL) was added slowly, the slurry was warmed to room temperature, and stirring was continued overnight. The organic layer was decanted and dried (MgSO₄). Solvent was removed to afford an off-white solid, compound 18A (2.5 g). MS: 165 (M+1)⁺.

Preparation of Toluene-4-sulfonic acid Chroman-3-ylmethyl ester (Compound 18B)

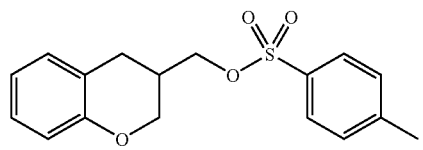

Compound 18A (3.6 g) was dissolved in pyridine (11 mL) at RT. Toluene sulfonyl chloride (4.5 g) was added, stirred for 6 h. The reaction mixture was quenched with 2N HCl (500 mL), ether extraction (2×200 mL). The combined ether was washed with water, brine, dried (MgSO₄), concentrated, to afford an orange color solid, compound 18B (4.2 g). mp 83–84° C.; MS: 319 (M+1)⁺.

Preparation of Chroman-3-yl-acetonitrile (Compound 18C)

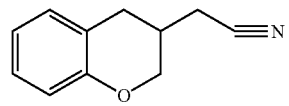

Compound 18B (1.25 g), NaCN (0.15 g) in 25 mL of DMF, were heated to 60° C. for 12 h. The solvent was removed, the reaction mixture was mixed with water (125 mL) and ether (125 mL). The ether layer was separated, washed with water, brine, dried (MgSO₄), concentrated to afford compound 18C (0.67 g). mp 54–55.5° C.; MS: 174 (M+1)⁺.

Preparation of 3-Cyanomethyl-chroman-6-sulfonyl chloride (Compound 18D)

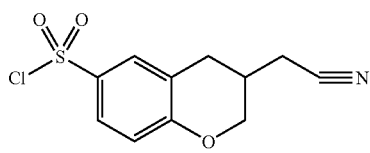

Compound 18D was prepared according to the method of example 1B utilizing compound 18C. The crude product was used immediately.

Preparation of 6-Mercapto-chroman-3-yl-acetonitrile (Compound 18E)

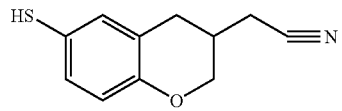

Compound 18E was prepared according to the method of example 1C utilizing compound 18D. Compound 18E was prepared in 35% yield. MS: 204 (M−1)⁺.

Preparation of 6-[4-Methyl-2-(4-trifluoromethyl-pheny)-thiazol-5-ylmethylsulfanyl]-chroman-3-yl-acetonitrile (Compound 18F)

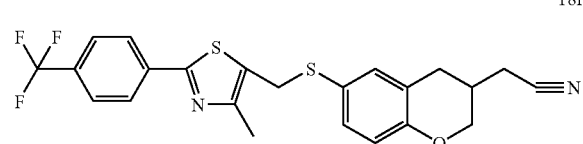

18F

Compound 18F was prepared according to the method of example 1D utilizing compound 18E. Compound 18F was prepared in 80% yield. MS: 461 (M+1)⁺.

Preparation of 6-[4-Methyl-2-(4-trifluoromethyl-pheny)-thiazol-5-ylmethylsulfanyl]-chroman-3-yl-acetic acid (Compound 18)

Compound 18F (1.5 g), MeOH (5 mL), THF (25 mL), 50% NaOH (5 mL), water (5 mL), were heated to reflux overnight. The solvent was removed. The crude reside was mixed with water (200 mL) and ether (200 mL). The mixture was acidified with 2N HCl to pH 2. The ether layer was separated, washed with water, brine, dried (MgSO₄), concentrated to give a oil product. The oil material was mixed with 20 mL of MeOH, stirred at RT till a white precipitate form. The solid was filtered to afford compound 18 (0.75 g). mp 149–149.5° C.;
MS: 480 (M+1)⁺.

EXAMPLE 19

Synthesis of {6-Methoxy-5-[4-methyl-2-(4-trifluoromethyl-phenyl)-thiazol-5-ylmethylsulfanyl]-indan-1-yl}-acetic acid (Compound 19)

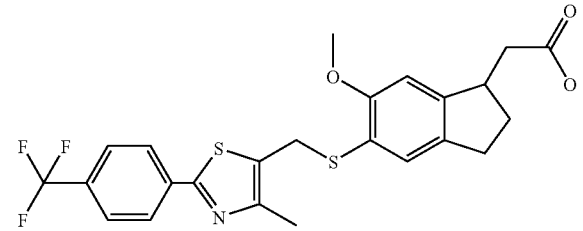

19

Preparation of (6-Methoxy-indan-1Yl)-acetic acid ethyl ester (Compound 19A)

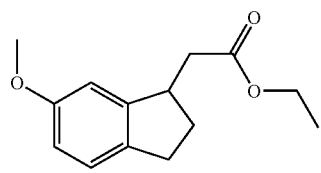

19A

6-Methoxy-1-indanone (5.0 g, 30.8 mmol) and triethyl phosphonoacetate (13.82 g, 61.6 mmol) in THF (15 ml) was added to a stirred solution of sodium hydride (2.46 g, 61.6 mmol) and ethanol (1.06 g, 23.1 mmol). The mixture was heated at 80° C. overnight. After removing the solvent in vacuo, the residue was diluted with water (50 ml) and layered with ether (50 ml). The layers were separated and the aqueous layer extracted with ether (2×25 ml). The combined organics were dried with MgSO₄ and condensed to give a crude dark oil. It was purified bysilica gel chromatography eluted with 10% EtOAc/Hexanes to afford the yellow solids in 39% yield.

Compound 19A was then prepared by hydrogenation of the unsaturated solid catalyzed by Pd/C (10%) in quantitative yield. MS: 235 (M+1)⁺.

Preparation of (5-chlorosulfonyl-6-Methoxy-indan-1-yl)-acetic acid ethyl ester (Compound 19B)

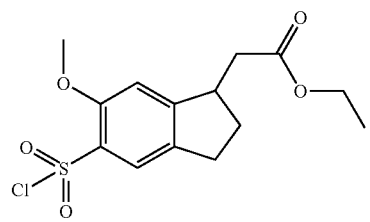

19B 19B was prepared analogously to compound 1B. 39% yield. MS: 333 (M+1)⁺.

Preparation of (5-Mercapto-6-methoxy-indan-1-yl)-acetic acid ethyl ester (Compound 19C)

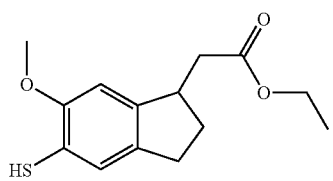

19C 19C was prepared analogouslyto compound 1C. Used as unpurified oil. MS: 267 (M+1)⁺.

Preparation of {6Methoxy-5-[4-Methyl-2-(4-trifluoromethyl-phenyl)-thiazol-5-ylmethylsulfanyl]-indan-1-yl}-acetic acid methyl ester (Compound 19D)

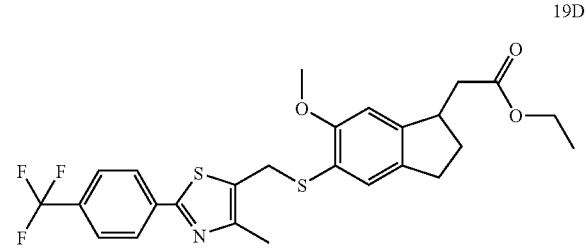

19D

Compound 19D was prepared analogously to compound 1D. Yield was 51% after flash column purification. MS: 522 (M+1)⁺.

Preparation of {6-Methoxy-5-[4-methyl-2-(4-trifluoromethyl-phenyl)-thiazol-5-ylmethylsulfanyl]-indan-1-yl}-acetic cid (Compound 19)

Compound 19 was prepared analogously to compound 1. Compound 19 was prepared in 14% yield. MS: 494 (M+1)⁺.

EXAMPLE 20

Synthesis of 6-[4-Methyl-2-(4-trifluoromethyl-pheny)-thiazol-5-ylmethylsulfanyl]-4-oxo-chroman-3-ylidene-acetic acid (Compound 20)

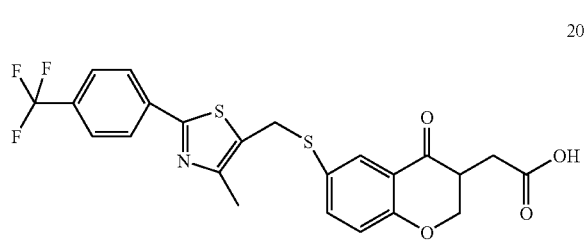

Preparation of 4-oxo-chroman-3-ylidene-acetic acid (Compound 20A)

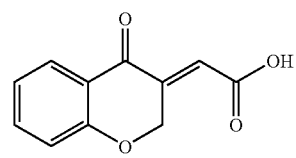

A solution of 4-chromanone (1.2 g), glyoxylic acid monohydrate (3 g), NaOH (1.6 g) in 5 mL of MeOH and 5 mL of water was heated to reflux for 2 h. The reaction mixture was concentrated, mixed with 25 mL of water, acidified with HCl till pH 2. The product was precipitated, filtered, washed with water, dried under vacuum to afford an off-white solid compound 20A (0.38 g). mp 134–136° C.; MS: 205(M+1)$^+$.

Preparation of 4-Oxo-chroman-3-yl-acetic acid methyl ester (Compound 20B)

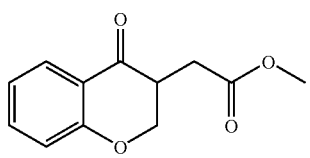

A solution of compound 20A (0.38 g), Tin powder (0.5 g), 1 mL of MeOH, 5 mL of 4N HCl in dioxane was heated to reflux for 2 h. The reaction mixture was cooled to 0° C., filtered the solid. The filtrate was mixed with 50 mL of ethyl acetate and 50 ml of water. The organic layer was separated, washed with water, brine, dried (MgSO$_4$). Concentrated to afford compound 20B (0.4 g). MS: 221 (M+1)$^+$.

Preparation of 6-chlorosulfonyl-4-oxo-chroman-3-yl-acetic acid methyl ester (Compound 20C)

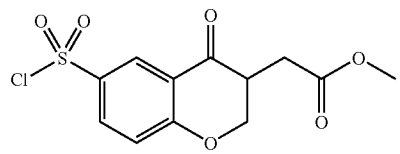

Compound 20C was prepared according to the method of example 1B utilizing compound 20B. The crude product was used immediately.

Preparation of 6-Mercapto-4-oxo-chroman-3-yl-acetic acid methyl ester (Compound 20D)

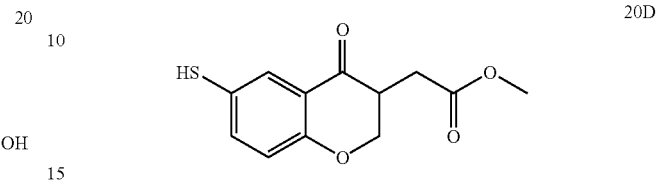

Compound 20D was prepared according to the method of example 1C utilizing compound 20C. Compound 20D was prepared in 75% yield. MS: 251 (M−1).

Preparation of 6-[4-Methyl-2-(4-trifluoromethyl-pheny)-thiazol-5-ylmethylsulfanyl]-4-oxo-chroman-3-ylidene-acetic acid methyl ester (Compound 20E)

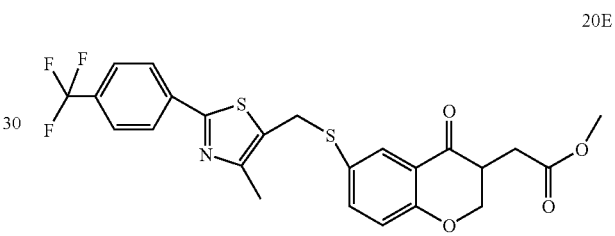

Compound 20E was prepared according to the method of example 1D utilizing compound 20D. Compound 20E was prepared in 65% yield. mp 93–94° C.; MS: 508 (M+1)$^+$.

Preparation of 6-[4-Methyl-2-(4-trifluoromethyl-pheny)-thiazol-5-ylmethylsulfanyl]-4-oxo-chroman-3-ylidene-acetic acid (Compound 20)

Compound 20 was prepared according to the method of example 1 utilizing compound 20E. Compound 20 was prepared in 10% yield. MS: 494 (M+1)$^+$.

EXAMPLE 21

Synthesis of 3-{5-[4-Methyl-2-(4-trifluoromethyl-pheny)-thiazol-5-ylmethylsulfanyl]-2,3-dihydro-indol-1-yl}-propionic acid (Compound 21)

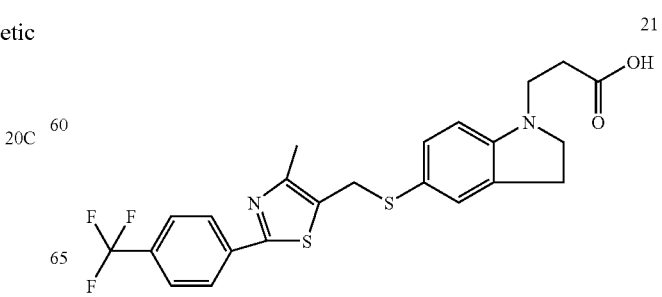

Preparation of 3-(2,3-dihydro-indol-1-yl)-propionic acid methyl ester (Compound 21A)

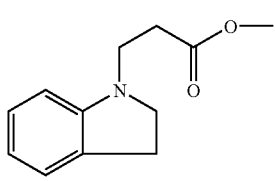

A solution of indoline (6.15 g), methyl 3-bromopropionate (13 g), potassium carbonate (21 g) in 150 mL of acetonitrie was refluxed fro 16 h. The reaction mixture was concentrated, mixed with 300 mL of ether. The mixed reaction solution was filtered, concentrated down to afford compound UUA (8 g). MS: 206 (M+1)$^+$.

Preparation of 3-(5-Thiocyanato-2,3-dihydro-indol-1-yl)-propionic acid methyl ester (Compound 21B)

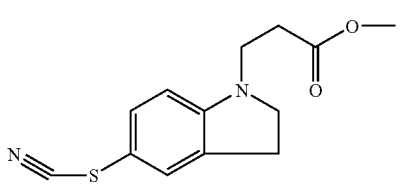

Compound 21B was prepared according to the method of example 14B utilizing compound 21A. Compound 21B was prepared in 80% yield. MS: 263 (M–1)$^+$.

Preparation of 3-(5-Mercapto-2,3-dihydro-indol-1-yl)-propionic acid methyl ester (Compound 21C)

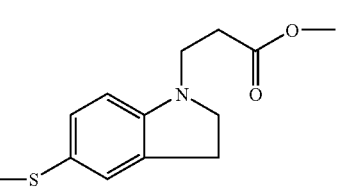

Sodium borohydride (0.6 g) was added to a solution of compound 21B (0.65 g) in 20 mL of MeOH at 0° C. by portion in 15 minutes period. The mixture was stirred for another 30 minutes at RT, quenched with 50 mL of water and 50 mL of ether. The organic layer was separated, washed with water, brine, dried (MgSO$_4$), concentrated to afford compound 21C (0.42 g). MS: 236 (M–1)$^+$.

Preparation of 3-{5-[4-Methyl-2-(4-trifluoromethyl-pheny)-thiazol-5-ylmethylsulfanyl]-2,3-dihydro-indol-1-yl}-propionic acid methyl ester (Compound 21D)

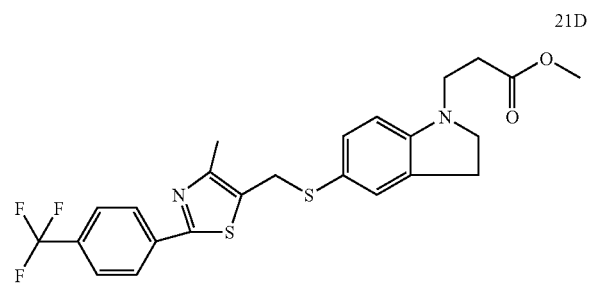

Compound 21D was prepared according to the method of example 1D utilizing compound 21C. Compound 21D was prepared in 20% yield. MS: 493 (M+1)$^+$.

Preparation of 3-{5-[4-Methyl-2-(4-trifluoromethyl-pheny)-thiazol-5-ylmethylsulfanyl]-2,3-dihydro-indol-1-yl}-propionic acid (Compound 21)

Compound 21 was prepared according to the method of example 1 utilizing compound 21D. Compound 21 was prepared in 60% yield. Mp 78–80° C.; MS: 479 (M+1)$^+$.

EXAMPLE 22

Synthesis of 6-Methoxy-5-[4-Methyl-2-(4-trifluoromethyl-pheny)-thiazol-5-ylmethylsulfanyl]-3-oxo-3H-benzo[d]isoxazo-2-yl-acetic-acid (Compound 22)

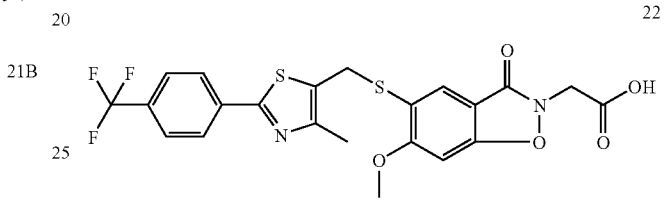

Preparation of 2, N-Dihydroxy-4-methoxy-benzamide (Compound 22A)

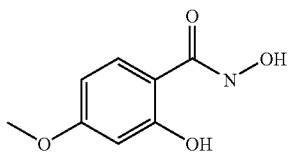

The 50%(w/w) NaOH (28 mL) was added to a solution of NH$_2$OH hydrochloride salt (13.9 g, 0.2 mole) in water (65 mL) by portion at RT. The 2-hydroxy-4-methoxy-benzoic acid methyl ester (18.2 g, 0.1 mole) in dioxane (50 mL) was added dropwise, another 6 h stirred at RT. The reaction mixture was concentrated, mixed with 300 mL of water, acidified with concentrated HCl till pH 5. The product was precipitated, filtered, washed with water and dried under vacuum, to afford an off-white solid compound 22A (17.3 g). MS: 184 (M+1)$^+$.

Preparation of 6-Methoxy-benzo[d]isoxazol-3-one (Compound 22B)

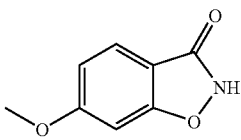

The 1,1'-carbonyldiimidazole (30.5 g) in 200 mL of THF was added dropwise to a refluxing solution of RRA (17.3 g) in 300 mL of THF, another 1.5 h at refluxing condition. The reaction mixture was concentrated, mixed with 400 mL of water, acidified with concentrated HCl till PH 2. The product was precipitated, filtered, washed with water, dried under vacuum, to afford an off-white solid compound RRB (6.1 g). MS: 166 (M+1)$^+$.

Preparation of 6-Methoxy-3-oxo-3H-benzo[d]isoxazol-2-yl-acetic acid methyl ester (Compound 22C)

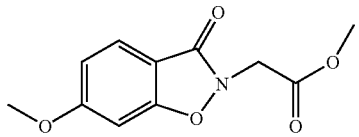

22C

The KN(TMS)$_2$ (7.2 g) was added to a solution of compound 22B (4 g) in 150 mL of THF at 0° C. by portion, another one hour at 0° C. with stirring. Methyl bromoacetate (7 g) was added, stirred at RT overnight. The reaction mixture was quenched with 150 mL of ethyl acetate and 100 mL of 2N HCl. The organic layer was separated, washed with water, brine, dried (MgSO$_4$), concentrated to afford an off-white solid compound 22C (2.5 g). mp 185–188° C.; MS: 238 (M+1)$^+$.

Preparation of 5-Chlorosulfonyl-6-methoxy-3-oxo-3H-benzo[d]isoxazol-2-yl-acetic acid methyl ester (Compound 22D)

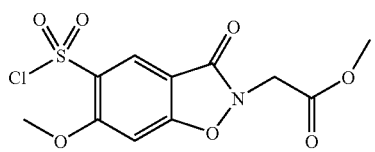

22D

Compound 22D was prepared according to the method of example 1B utilizing compound 22C. The crude product was used immediately.

Preparation of 5-Mercapto-6-methoxy-3-oxo-3H-benzo[d]isoxazol-2-yl-acetic acid methyl ester (Compound 22E)

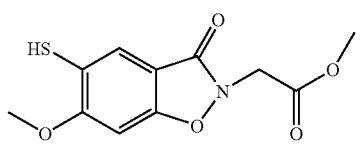

22E

Compound 22E was prepared according to the method of example 1C utilizing compound 22D. Compound 22E was prepared in 10% yield. MS: 268 (M−1)$^+$.

Preparation of 6-Methoxy-5-[4-methyl-2-(4-trifluoromethyl-phenyl)-thiazol-5-ylmethylsulfanyl]-3-oxo-3H-benzo[d]isoxazol-2-yl-acetic acid methyl ester (Compound 22F)

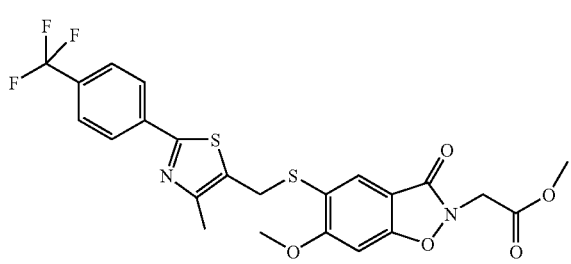

22F

Compound 22F was prepared according to the method of example 1D utilizing compound 22E. Compound 22F was prepared in 10% yield. MS: 525 (M+1)$^+$.

Preparation of 6-Methoxy-5-[4-methyl-2-(4-trifluoromethyl-pheny)-thiazol-5-ylmethylsulfanyl]-3-oxo-3H-benzo[d]isoxazo-2-yl-acetic acid (Compound 22)

Compound 22 was prepared according to the method of example 1 utilizing compound 22F. Compound 22 was prepared in 50% yield. mp 245–247° C.; MS: 511 (M+1)$^+$.

EXAMPLE 23

Synthesis of {6-[4-methyl-2-(4-trifluoromethyl-phenyl)-thiazol-5-ylmethoxy]-benzo[b]thiophen-3-acetic acid (compound 23)

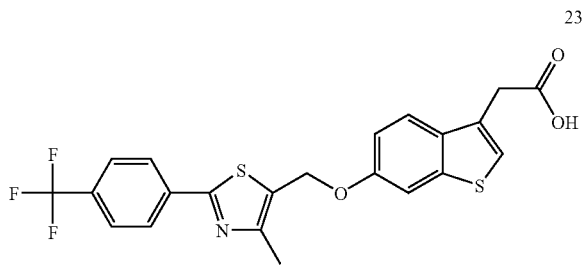

23

Preparation of 4-(3-(3-Methoxy-phenylsulfanyl)-3-oxo-butyric acid methyl ester (compound 23A)

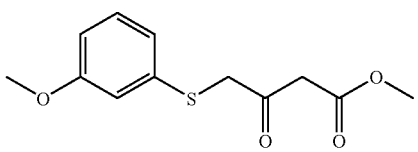

23A

A solution of methyl 2-chloroacetoacetate (15.0 g, 0.10 mol) in 20 ml of acetonitrile was added dropwise to a mixture of 3-methoxythiophenol (14.0 g, 0.10 mol) and cesium carbonate (65.2 g, 0.20 mol) in 400 ml of acetonitrile over 30 min. The mixture was stirred at room temperature for 2 hours, then filtered through Celite®. The filtrate was concentrated and purified using normal phase chromatography. 400 MHz $^1$H NMR (CDCl$_3$) δ 7.21 (dt, 1H), 6.95–6.85 (m, 2H), 6.78 (dd, 1H), 3.82 (s, 2H), 3.80 (s, 3H), 3.65 (s, 2H), MS (ES (M−1)=253).

Preparation of (6-methoxybenzo[b]thiophen-3-yl)acetic acid methyl ester (compound 23B)

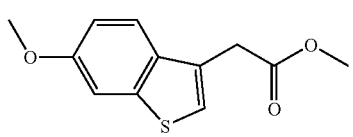

23B

The product from example 23A (2.54 g, 0.01 mol) was added dropwise to 25 ml of methanesulfonic acid at room temperature, and the solution was stirred at the same temperature for 15 minutes, then the reaction mixture was added to 250 ml of ice-water. The aqueous mixture was extracted with ethyl acetate. The organic phase was washed with brine, sodium bicarbonate, dried over sodium sulfate, and concentrated to give 23B in good purity. 400 MHz $^1$H NMR (CDCl$_3$) δ 7.64 (d. 1H). 7.32 (d. 1H). 7.18 (s. 1H). 7.04 (dd, 1H), 3.88 (s, 3H), 3.82 (s, 2H), 3.71 (s, 3H). MS (ES (M+1)=236).

Preparation of (6-Hydroxy-benzo[b]thiophen-3-yl)acetic acid methyl ester (compound 23C)

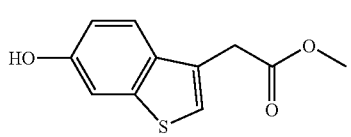

23C

To a stirred solution of the product from example 23B (2.20 g, 9.32 mmol) in 50 ml of dichloromethane at −78° C. was added dropwise a solution of boron tribromide (11.68 g, 46.6 mmol) in 50 ml of dichloromethane. After the completion of the addition of boron tribromide, the reaction mixture was maintained at −78° C. for 1 h, then allowed to reach room temperature and stirred at the same temperature overnight. The mixture was cooled to 0° C., carefully quenched with 100 ml of water, extracted with ethyl acetate, washed with brine, dried over sodium sulfate, concentrated, and purified using normal phase chromatography to afford the title product. 400 MHz $^1$H NMR (CDCl$_3$) δ 7.59 (d, 1H), 7.25 (d, 1H), 7.16 (s, 1H), 6.92 (dd, 1H), 5.20 (brs, 1H), 3.82 (s, 2H), 3.71 (ES (M+1)=223).

Preparation of {6-[4-Methyl-2-(4-trifluoromethyl-phenyl)-thiazol-5-ylmethoxy]-benzo[b]thiophen-3-yl}-acetic acid methyl ester (compound 23D)

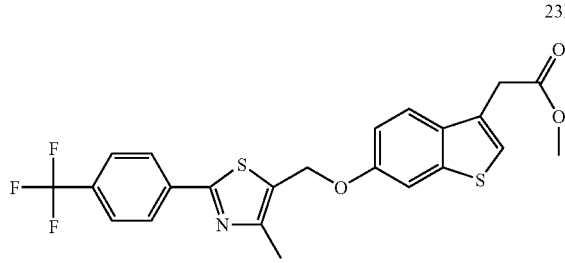

23D

The title compound was prepared from compound 23C in a manner analogous to compound 6E. MS m/z 478 (M+1).

Preparation of {6-[4-Methyl-2-(4-trifluoromethyl-phenyl)-thiazol-5-ylmethoxy]-benzo[b]thiophen-3-yl}-acetic acid (compound 23)

The title compound was prepared from compound 23D in a manner analogous to compound 6. MS m/z 464 (M+1).

EXAMPLE 24

Synthesis of {5-[4-Methyl-2-(4-trifluoromethyl-phenyl)-thiazol-5-ylmethoxy]-indol-1-yl}-acetic acid (compound 24)

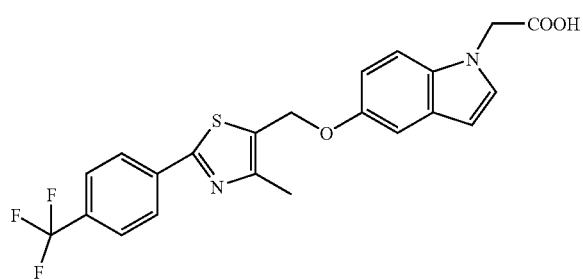

24

Preparation of 5-[4-Methyl-2-(4-trifluoromethyl-phenyl)-thiazol-5-ylmethoxy]-1H-indole (compound 24A)

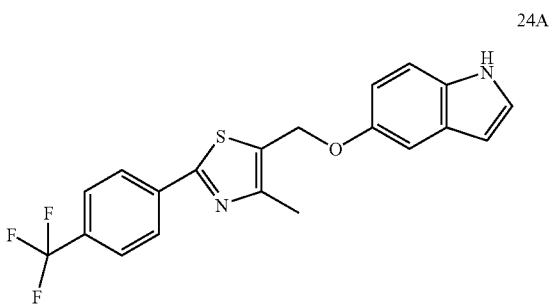

24A

5-Hydroxyindole (200 mg, 1.5 mmol) was dissolved in acetonitrile (10 mL) with the chloride 5-chloromethyl-4-methyl-2-(4-trifluoromethyl-phenyl)-thiazole (0.50 g, 1.7 mmol) and Cs$_2$CO$_3$ (2.37 g, 7.27 mmol) The reaction mixture was stirred at RT overnight. Ether (50 mL) and H$_2$O were added and stirring was continued for another 5 min. The layers were separated and the aqueous layer was extracted with ether (2×100 mL). The combined organics was dried over MgSO$_4$ and concentrated. The crude product was purified by column chromatography eluted with EtOAc and hexanes to give the desired product as a white solid (0.3 g, 51% yield).

MS m/z 389 (M+1)$^+$.

Preparation of {5-[4-Methyl-2-(4-trifluoromethyl-phenyl)-thiazol-5-ylmethoxy]-indol-1-yl}-acetic acid methyl ester (compound 24B)

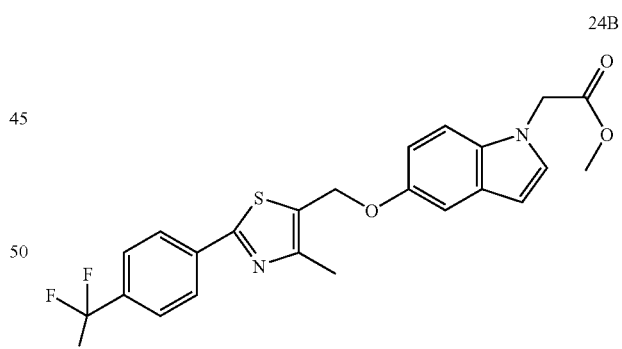

24B

Compound 24B was made from Compound 24A in the same way as 10A in 56% yield.

MS m/z 461 (M+1)$^+$.

Preparation of {5-[4-Methyl-2-(4-trifluoromethyl-phenyl)-thiazol-5-ylmethoxy]-indol-1-yl}-acetic acid (compound 24)

Compound 24 was prepared according to the method of example 1 utilizing compound 24B. Compound X was prepared in 72% yield. MS m/z 447 (M−1)$^{30}$.

EXAMPLE 25

Synthesis of {5-[4-methyl-2-(4-trifluoromethyl-phenyl)-thiazol-5-ylmethylsulfanyl]-indol-1-yl}-acetic acid (Compound 25)

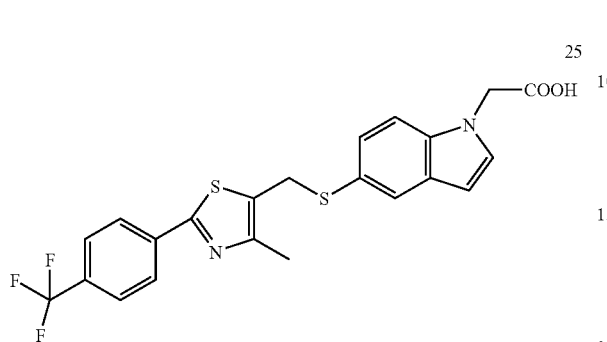

Preparation of (2,3-dihydro-indol-1-yl)-acetic acid methyl ester (compound 25A)

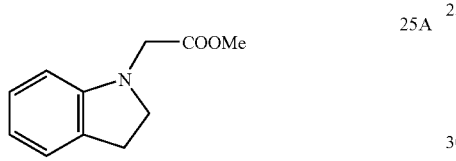

Compound 25A was prepared analogously to compound 10A in 66% yield.
MS m/z 192 (M+1)$^+$.

Preparation of (5-Thiocyanato-2,3-dihydro-indol-1-yl)-acetic acid methyl ester (compound 25B)

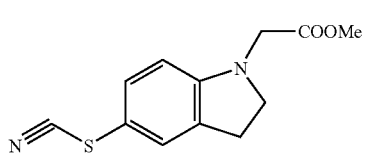

Compound 25B was prepared analogously to compound 14B in 40% yield.
MS m/z 249 (M+1)$^+$.

Preparation of (5-Mercapto-2,3-dihydro-indol-1-yl)-acetic acid methyl ester (compound 25C)

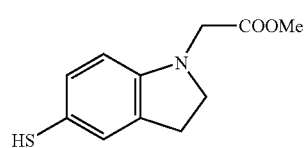

Compound 25B (1.05 g, 4.2 mmol) was refluxed in a solution of water (2 ml), methanol (20 ml) and mercaptoacetic acid (1.2 g, 13 mmol) for 3 h. The solvent was removed under the vacuo, and the crude product was passed a short silica gel chromatography to give 25C in 95% yield.
MS m/z 224 (M+1)$^+$.

Preparation of {5-[4-Methyl-2-(4-trifluoromethyl-phenyl)-thiazol-5-ylmethylsulfanyl]-2,3-dihydro-indol-1-yl}-acetic acid methyl ester (compound 25D)

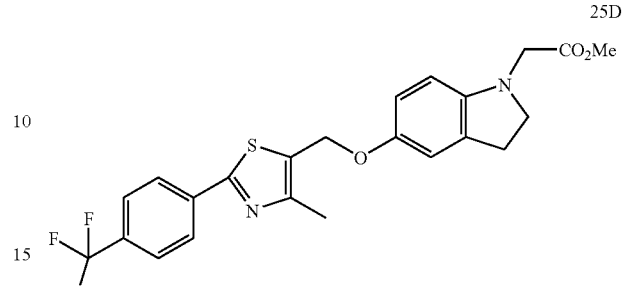

Compound 25D was made from compound 25C the same way as compound 1D in 31% yield. MS m/z 479 (M+1)$^+$.

Preparation of {5-[4-Methyl-2-(4-trifluoromethyl-phenyl)-thiazol-5-ylmethylsulfanyl]-indol-1-yl}-acetic acid methyl ester (compound 25E)

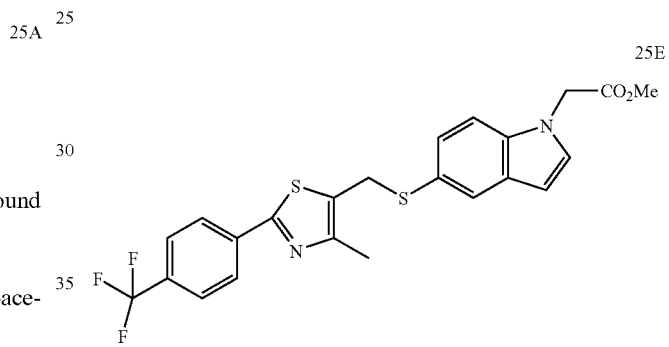

Compound 25D (600 mg, 1.3 mmol), and tetrachloro-1,2-benzoquinone (300 mg, 1.3 mmol) were stirred in 10 ml anhydrous ether at RT for 1 h. The compound 25E was purified using normal phase chromatography in 15% yield.
MS m/z 447 (M−1)$^+$.

Preparation of {5-[4-Methyl-2-(4-trifluoromethyl-phenyl)-thiazol-5-ylmethylsulfanyl]-indol-1-yl}-acetic acid (compound 25)

Compound 25 was prepared according to the method of example 1 utilizing compound 25E. Compound 25 was prepared in 97% yield. MS m/z 463 (M−1)$^+$.

BIOLOGICAL ASSAYS

The compounds of the present invention have demonstrated PPAR modulating activity in the standard assays commonly employed by those skilled in the art. Accordingly, such compounds and formulations comprising such compounds are useful for treating, preventing or controlling dyslipidemia in a mammal.

A. Selectivity Measurements

1. Test A. Transient Transfections Assay Using the HepG2 Hepatoma Cell Line.

HepG2 cells were transiently transfected with an expression plasmids encoding hPPARα, hPPARβ or mPPARγ chimeric receptors and a reporter containing the yeast upstream activating sequence (UAS) upstream of the viral E1B promoter controlling a luciferase reporter gene. In addition, the plasmid pRSVβ-gal was used to control for transfection efficiency. HepG2 cells were grown in DMEM supplemented with 10% FBS and 1 μM non-essential amino acid. On the first day, cells were split into 100 mm dishes at $2.5 \times 10^6$/dish and incubated overnight at $37C.°/5\%$ $CO_2$. On the second day the cells were transiently transfected with plasmid DNA encoding a chimeric receptor, the luciferase reporter gene; and β-gal. For each 100 mm dish, 15 μg of lucifease reporter (PG5E1b) DNA, 15 μg of Gal4-pPAR chimeric receptor DNA, and 1.5 μg of μ-gal plasmid DNA were mixed with 1.4 ml of opti-MEM in the tube. 28 μl of LipoFectamine-2000 reagent was added to 1.4 ml of opti-MEM in the tube, and incubate for 5 min at RT. The diluted Lipofectamine-2000 reagent was combined with the DNA mixture, and incubate for 20 min at RT. After fresh medium was added to each 100 mm dish of cells, 2.8 ml of Lipofectamine2000-DNA mixture was added dropwise to the 100 mm dish containing 14 ml of medium, and incubate 37° C. overnight. On day three cells were trypsinized off the 100 mm dishes and re-plated on 96 well plates. Cells were plated at $2.5 \times 10^4$ cells per well in 150 μl of media and 50 μl of compound diluted by media was added. The concentrations of reference agents and test compound added were in the range from 50 μM to 50 pM. After addition of compounds, the plates were incubated at 37° C. for 24 hours. Subsequently cells were washed once with 100 μl of PBS, lysed, and processed for measuring luciferase and μ-gal activity using Dual-Light luciferase kit from Tropix®, according to the manufacturer's recommendations, on an EG&G Bethold MicroLumat LB96P luminometer. $EC_{50}$ values were obtained using the GraphPad Prism™ program. Surprisingly, the compounds of the present invention exhibit activity for both PPARα and PPARβ. Accordingly, the compounds of the present invention should find considerable therapeutic applications for hypercholesterolemia and hyperlipidemia. The Hep G2-hBeta $EC_{50}$ ("$EC_{50}β$") data as well as the Hep G2-hAlpha $IEC_{50}$ ("$EC_{50}α$") data of the compounds of the invention are presented in Table 1 below.

TABLE 1

| Example | Hep G2-hβ $EC_{50}$ nM | Hep G2-hα $EC_{50}$ nM |
|---|---|---|
| 1 | 177.7 | 384 |
| 2 | 267.4 | 1957 |
| 3 | 762.0 | 917 |
| 4 | 1542 | 899 |
| 5 | 8.3 | 3737.75 |
| 6 | 2000000 | 2044 |
| 7 | 614.0 | — |
| 8 | 3470.0 | — |
| 9 | 2000000 | — |
| 10 | 111.1 | — |
| 11 | 286.0 | 1928 |
| 12 | 896.1 | 2000000 |
| 13 | 24.1 | 1190 |
| 14 | 19.0 | 2000000 |
| 15 | 252.2 | 1301 |
| 16 | 2210.0 | — |
| 17 | 2130.0 | 2185 |
| 18 | 394.0 | 1002254.5 |
| 19 | 113.0 | 42 |
| 20 | — | — |
| 21 | — | — |
| 22 | 2000000 | — |
| 23 | 1.7 | 572.0 |
| 24 | — | — |
| 25 | — | — |

FORMULATIONS

The compounds of the present invention can be administered alone or in combination with one or more therapeutic agents. These include, for example, other agents for treating, preventing or controlling dyslipidemia, non-insulin dependent diabetes mellitus, obesity, hyperglycemia, hypercholesteremia, hyperlipidemia, atherosclerosis, hypertriglyceridemia, or hyperinsulinemia.

The compounds are thus well suited to formulation for convenient administration to mammals for the prevention and treatment of such disorders.

The following examples further illustrate typical formulations provided by the invention.

| Formulation 1 | |
|---|---|
| Ingredient | Amount |
| compound of Formulas 1–50 | 0.5 to 800 mg |
| sodium benzoate | 5 mg |
| isotonic saline | 1000 mL |

The above ingredients are mixed and dissolved in the saline for IV administration to a patient.

| Formulation 2 | |
|---|---|
| Ingredient | Amount |
| compound of Formulas 1–50 | 0.5 to 800 mg |
| cellulose, microcrystalline | 400 mg |
| stearic acid | 5 mg |
| silicon dioxide | 10 mg |
| sugar, confectionery | 50 mg |

The ingredients are blended to uniformity and pressed into a tablet that is well suited for oral administration to a patient.

| Formulation 3 | |
|---|---|
| Ingredient | Amount |
| compound of Formulas 1–50 | 0.5 to 800 mg |
| starch, dried | 250 mg |
| magnesium stearate | 10 mg |

The ingredients are combined and milled to afford material suitable for filling hard gelatin capsules administered to a patient.

| Formulation 4 | |
|---|---|
| Ingredient | Amount % wt./(total wt.) |
| compound of Formulas 1–50 | 1 to 50 |
| Polyethylene glycol 1000 | 32 to 75 |
| Polyethylene glycol 4000 | 16 to 25 |

The ingredients are combined via melting and then poured into molds containing 2.5 g total weight.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A compound having formula 1:

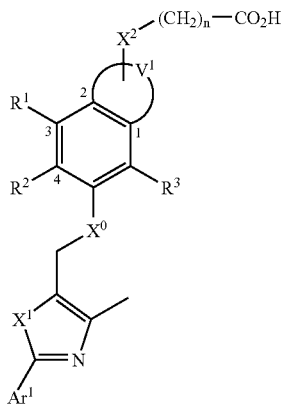

or a pharmaceutically acceptable salt thereof, wherein:
$V^1$ is a hydrocarbon-heteroatom chain, said heteroatom being one nitrogen said chain having from 3 to 4 atoms wherein the carbon atom of position 1 is connected to the carbon atom of position 2 to form a five to six member ring wherein the

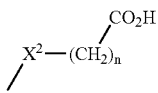

is attached to a substitutionally available position of said ring;
$X^0$ is O or S;
$X^1$ is S;
$X^2$ is absent;
$Ar^1$ is substituted or unsubstituted aryl;
$R^1$, $R^2$ and $R^3$ are independently hydrogen, lower alkyl, lower alkoxy, lower thioalkoxy, —O(CH$_2$)$_p$CF$_3$, halogen, nitro, cyano, —OH, —SH, —CF$_3$, S(O)$_p$Alkyl, S(O)$_p$Aryl, —(CH$_2$)$_m$OR$^4$, or —(CH$_2$)$_m$NR$^5$R$^6$, COR$^4$, —CO$_2$H, —CO$_2$R$^4$, or —NR$^5$R$^6$;
$R^4$ is hydrogen, alkyl, alkenyl, alkynyl, or aryl;
$R^5$ and $R^6$ are independently hydrogen, alkyl, alkenyl, alkynyl, cycloalkyl, SO$^2$Alkyl or, SO$^2$Aryl;
m is 0 to 5;
n is 0 to 5; and
p is 0 to 2.

2. The compound of claim 1, wherein:
$R^1$, $R^2$, and $R^3$ are independently hydrogen, alkyl, or alkoxy.

3. The compound of claim 1, wherein:
$R^1$ and $R^3$ are hydrogen; and
$R^2$ is alkyl or alkoxy.

4. The compound of claim 1, wherein:
$R^1$ and $R^3$ are hydrogen; and
$R^2$ is alkoxy.

5. The compound of claim 1, wherein:
$R^1$ and $^3$ are independently hydrogen, methyl, ethyl, isopropyl, n-propyl, t-butyl, n-butyl, or isobutyl; and
$R^2$ is methyoxy, ethoxy, isopropoxy, n-propoxy, t-butoxy, n-butoxy, or isobutoxy.

6. A pharmaceutical composition comprising a compound of claim 1 and one or more carriers, diluents, or excipients.

7. A compound selected from:
{6-[4-Methyl-2-(4-trifluoromethyl-phenyl)-thiazol-5-yl-methylsulfanyl]-3,4-dihydro-1H-isoquinolin-2-yl}-acetic acid;
{6-[4-Methyl-2-(4-trifluoromethyl-phenyl)-thiazol-5-yl-methylsulfanyl]-3,4-dihydro-2H-quinolin-1-yl}-acetic acid;
{6-[4-Methyl-2-(4-trifluoromethyl-pheny)-thiazol-5-yl-methylsulfanyl]-2-oxo-3,4-dihydro-2H-isoquinolin-1-yl}-acetic acid;
3-{5-[4-Methyl-2-(4-trifluoromethyl-pheny)-thiazol-5-ylmethylsulfanyl]-2,3-dihydro-indo-1-yl}-propionic acid;
{5-[4-Methyl-2-(4-trifluoromethyl-phenyl)-thiazol-5-yl-methoxy]-indol-1-yl}-acetic acid; and
{5-[4-Methyl-2-(4-trifluoromethyl-phenyl)-thiazol-5-yl-methylsulfany]-indol-1-yl}-acetic acid; and
pharmaceutically acceptable salts thereof.

8. A compound selected from:
{4-Methyl-5-[4-methyl-2-(4-trifluoromethyl-phenyl)-thiazol-5-ylmethoxy]-indol-1-yl}-acetic acid;
{2-Methyl-5-[4-methyl-2-(4-trifluoromethyl-phenyl)-thiazol-5-ylmethoxy]-indol-1-yl}-acetic acid;
{3-Methyl-5-[4-methyl-2-(4-trifluoromethly-phenyl)-thiazol-5-ylmethoxy]-indol-1-yl}-acetic acid;
{6-Methoxy-5-[4-methyl-2-(4-trifluoromethyl-phenyl)-thiazol-5-ylmethoxy]-indol-1-yl}-acetic acid;
1-carboxymethyl-2-methyl-5-[4-methyl-2-(4-tifluoromethyl-phenyl)-thiazol-5-ylmethoxy)-1H-indole-3-carboxylic acid ethyl ester;
{6-[4-Methyl-2-(4-trifluoromethyl-phenyl)-thiazols-5-yl-methoxy]-1H-indol-3-yl}-acetic acid;
{1-Methyl-6-[4-methyl-2-(4-trifluoromethyl-phenyl)-thiazol-5-ylmethoxy]-1H-indol-3-yl}-acetic acid; and
{5-Methoxy-1-methyl-6-[4-methyl-2-(4-trifluoromethyl-phenyl)-thiazol-5-ylmethylsulfanyl]-1H-indol-3-yl}-acetic acid;
pharmaceutically acceptable salt thereof.

* * * * *